United States Patent
Rajeev et al.

(10) Patent No.: US 10,029,955 B1
(45) Date of Patent: Jul. 24, 2018

(54) CAPSULE FOR HIGH PRESSURE, HIGH TEMPERATURE PROCESSING OF MATERIALS AND METHODS OF USE

(71) Applicant: SLT TECHNOLOGIES, INC., Los Angeles, CA (US)

(72) Inventors: Pakalapati Tirumala Rajeev, Santa Barbara, CA (US); Douglas Wayne Pocius, Santa Barbara, CA (US); Derrick S. Kamber, Goleta, CA (US); Michael Coulter, Santa Barbara, CA (US)

(73) Assignee: SLT TECHNOLOGIES, INC., Los Angeles, CA (US)

( * ) Notice: Subject to any disclaimer, the term of this patent is extended or adjusted under 35 U.S.C. 154(b) by 891 days.

(21) Appl. No.: 13/657,551

(22) Filed: Oct. 22, 2012

Related U.S. Application Data

(60) Provisional application No. 61/550,794, filed on Oct. 24, 2011.

(51) Int. Cl.
| | |
|---|---|
| C30B 7/10 | (2006.01) |
| C30B 19/08 | (2006.01) |
| C07B 33/00 | (2006.01) |
| C30B 35/00 | (2006.01) |
| C30B 29/38 | (2006.01) |
| B01J 21/06 | (2006.01) |

(52) U.S. Cl.
CPC .............. *C07B 33/00* (2013.01); *C30B 35/00* (2013.01); *B01J 21/06* (2013.01); *C30B 7/10* (2013.01); *C30B 29/38* (2013.01)

(58) Field of Classification Search
CPC ..................................................... B01J 3/008
See application file for complete search history.

(56) References Cited

U.S. PATENT DOCUMENTS

| | | | |
|---|---|---|---|
| 4,030,966 A | 6/1977 | Hornig et al. | |
| 4,066,868 A | 1/1978 | Witkin et al. | |
| 4,350,560 A | 9/1982 | Helgeland et al. | |
| 5,098,673 A | 3/1992 | Engel et al. | |
| 5,169,486 A | 12/1992 | Young et al. | |
| 5,474,021 A | 12/1995 | Tsuno et al. | |
| 6,129,900 A | 10/2000 | Satoh et al. | |
| 6,273,948 B1 | 8/2001 | Porowski et al. | |
| 6,398,867 B1 | 6/2002 | D'Evelyn et al. | |
| 6,406,540 B1 | 6/2002 | Harris et al. | |
| 6,528,427 B2 | 3/2003 | Chebi et al. | |
| 6,533,874 B1 | 3/2003 | Vaudo et al. | |
| 6,596,079 B1 | 7/2003 | Vaudo et al. | |
| 6,639,925 B2 | 10/2003 | Niwa et al. | |
| 6,656,615 B2 | 12/2003 | Dwilinski et al. | |
| 6,686,608 B1 | 2/2004 | Takahira | |
| 6,764,297 B2 | 7/2004 | Godwin et al. | |
| 6,765,240 B2 | 7/2004 | Tischler et al. | |
| 6,784,463 B2 | 8/2004 | Camras et al. | |
| 6,787,814 B2 | 9/2004 | Udagawa | |
| 6,858,882 B2 | 2/2005 | Tsuda et al. | |
| 6,861,130 B2 | 3/2005 | D'Evelyn et al. | |
| 6,887,144 B2 | 5/2005 | D'Evelyn et al. | |
| 7,001,577 B2 | 2/2006 | Zimmerman et al. | |
| 7,012,279 B2 | 3/2006 | Wierer, Jr. et al. | |
| 7,026,756 B2 | 4/2006 | Shimizu et al. | |
| 7,053,413 B2 | 5/2006 | D'Evelyn et al. | |
| 7,063,741 B2 | 6/2006 | D'Evelyn et al. | |
| 7,078,731 B2 | 7/2006 | D'Evelyn et al. | |
| 7,098,487 B2 | 8/2006 | D'Evelyn et al. | |
| 7,112,829 B2 | 9/2006 | Picard et al. | |
| 7,119,372 B2 | 10/2006 | Stokes et al. | |
| 7,125,453 B2 | 10/2006 | D'Evelyn et al. | |
| 7,160,531 B1 | 1/2007 | Jacques et al. | |
| 7,170,095 B2 | 1/2007 | Vaudo et al. | |
| 7,175,704 B2 | 2/2007 | D'Evelyn et al. | |
| 7,198,671 B2 | 4/2007 | Ueda | |
| 7,252,712 B2 | 8/2007 | Dwilinski et al. | |
| 7,279,040 B1 | 10/2007 | Wang | |
| 7,285,801 B2 | 10/2007 | Eliashevich et al. | |
| 7,316,746 B2 | 1/2008 | D'Evelyn et al. | |
| 7,368,015 B2 | 5/2008 | D'Evelyn et al. | |
| 7,381,391 B2 | 6/2008 | Spencer et al. | |
| 7,420,261 B2 | 9/2008 | Dwilinski et al. | |
| 7,569,206 B2 | 8/2009 | Spencer et al. | |

(Continued)

FOREIGN PATENT DOCUMENTS

| | | |
|---|---|---|
| CN | 101061570 | 10/2007 |
| JP | 2005289797 | 10/2005 |

(Continued)

OTHER PUBLICATIONS

Roder et al., 'Temperature dependence of the thermal expansion of GaN', Physics Review B, vol. 72., No. 085218, Aug. 24, 2005, 6 pages.
USPTO Office Action for U.S. Appl. No. 13/013,697 dated Jun. 9, 2014 (5 pages).
USPTO Office Action for U.S. Appl. No. 13/041,199 dated Apr. 29, 2014 (12 pages).
Communication from the Chinese Patent Office re 200980154756.9 dated Jun. 17, 2014 (10 pages).
USPTO Office Action for U.S. Appl. No. 12/484,095 dated Aug. 29, 2014 (10 pages).
USPTO Notice of Allowance for U.S. Appl. No. 13/013,697 dated Aug. 27, 2014 (5 pages).
USPTO Notice of Allowance for U.S. Appl. No. 13/041,199 dated Sep. 9, 2014 (9 pages).

(Continued)

*Primary Examiner* — Yun Qian
(74) *Attorney, Agent, or Firm* — Patterson & Sheridan, LLP

(57) ABSTRACT

An improved capsule and method of use for processing materials or growing crystals in supercritical fluids is disclosed. The capsule is scalable up to very large volumes and provides for cost-effective processing. In conjunction with suitable high pressure apparatus, the capsule is capable of processing materials at pressures and temperatures of up to approximately 8 GPa and 1500° C., respectively.

24 Claims, 9 Drawing Sheets

(56) References Cited

U.S. PATENT DOCUMENTS

| | | |
|---|---|---|
| 7,625,446 B2 | 12/2009 | D'Evelyn et al. |
| 7,642,122 B2 | 1/2010 | Tysoe et al. |
| 7,704,324 B2 | 4/2010 | D'Evelyn et al. |
| 7,705,276 B2 | 4/2010 | Giddings et al. |
| 7,759,710 B1 | 7/2010 | Chiu et al. |
| 7,871,839 B2 | 1/2011 | Lee et al. |
| 7,976,630 B2 | 7/2011 | Poblenz et al. |
| 8,021,481 B2 | 9/2011 | D'Evelyn |
| 8,048,225 B2 | 11/2011 | Poblenz et al. |
| 8,097,081 B2 | 1/2012 | D'Evelyn |
| 8,148,801 B2 | 4/2012 | D'Evelyn |
| 8,188,504 B2 | 5/2012 | Lee |
| 8,198,643 B2 | 6/2012 | Lee et al. |
| 8,207,548 B2 | 6/2012 | Nagai |
| 8,278,656 B2 | 10/2012 | Mattmann et al. |
| 8,284,810 B1 | 10/2012 | Sharma et al. |
| 8,299,473 B1 | 10/2012 | D'Evelyn et al. |
| 8,303,710 B2 | 11/2012 | D'Evelyn |
| 8,306,081 B1 | 11/2012 | Schmidt et al. |
| 8,323,405 B2 | 12/2012 | D'Evelyn |
| 8,329,511 B2 | 12/2012 | D'Evelyn |
| 8,354,679 B1 | 1/2013 | D'Evelyn et al. |
| 8,430,958 B2 | 4/2013 | D'Evelyn |
| 8,435,347 B2 | 5/2013 | D'Evelyn et al. |
| 8,444,765 B2 | 5/2013 | D'Evelyn |
| 8,461,071 B2 | 6/2013 | D'Evelyn |
| 8,465,588 B2 | 6/2013 | Poblenz et al. |
| 8,482,104 B2 | 7/2013 | D'Evelyn et al. |
| 8,492,185 B1 | 7/2013 | D'Evelyn et al. |
| 8,729,559 B2 | 5/2014 | Krames et al. |
| 2001/0009134 A1 | 7/2001 | Kim et al. |
| 2001/0011935 A1 | 8/2001 | Lee et al. |
| 2001/0048114 A1 | 12/2001 | Morita et al. |
| 2002/0070416 A1 | 6/2002 | Morse et al. |
| 2002/0105986 A1 | 8/2002 | Yamasaki |
| 2002/0182768 A1 | 12/2002 | Morse et al. |
| 2002/0189532 A1 | 12/2002 | Motoki et al. |
| 2003/0027014 A1 | 2/2003 | Johnson et al. |
| 2003/0140845 A1 | 7/2003 | D'Evelyn et al. |
| 2003/0141301 A1* | 7/2003 | D'Evelyn ............... B01J 3/008 220/62.11 |
| 2003/0145784 A1 | 8/2003 | Thompson et al. |
| 2003/0164507 A1 | 9/2003 | Edmond et al. |
| 2003/0183155 A1 | 10/2003 | D'Evelyn et al. |
| 2003/0209191 A1 | 11/2003 | Purdy |
| 2003/0232512 A1 | 12/2003 | Dickinson et al. |
| 2004/0000266 A1 | 1/2004 | D'Evelyn et al. |
| 2004/0023427 A1 | 2/2004 | Chua et al. |
| 2004/0124434 A1* | 7/2004 | D'Evelyn ............... B82Y 10/00 257/103 |
| 2004/0124435 A1 | 7/2004 | D'Evelyn |
| 2004/0161222 A1 | 8/2004 | Niida et al. |
| 2004/0245535 A1 | 12/2004 | D'Evelyn et al. |
| 2005/0087753 A1 | 4/2005 | D'Evelyn et al. |
| 2005/0098095 A1 | 5/2005 | D'Evelyn et al. |
| 2005/0109240 A1 | 5/2005 | Maeta et al. |
| 2005/0121679 A1 | 6/2005 | Nagahama et al. |
| 2005/0128469 A1 | 6/2005 | Hall et al. |
| 2005/0152820 A1 | 7/2005 | D'Evelyn et al. |
| 2005/0167680 A1 | 8/2005 | Shei et al. |
| 2005/0205215 A1 | 9/2005 | Giddings et al. |
| 2005/0263791 A1 | 12/2005 | Yanagihara et al. |
| 2006/0021582 A1 | 2/2006 | Saito et al. |
| 2006/0032428 A1 | 2/2006 | Dwilinski et al. |
| 2006/0037529 A1 | 2/2006 | D'Evelyn et al. |
| 2006/0037530 A1 | 2/2006 | Dwilinski et al. |
| 2006/0048699 A1 | 3/2006 | D'Evelyn et al. |
| 2006/0096521 A1 | 5/2006 | D'Evelyn et al. |
| 2006/0118799 A1 | 6/2006 | D'Evelyn et al. |
| 2006/0124051 A1 | 6/2006 | Yoshioka et al. |
| 2006/0163589 A1 | 7/2006 | Fan et al. |
| 2006/0169993 A1 | 8/2006 | Fan et al. |
| 2006/0177362 A1* | 8/2006 | D'Evelyn ............... B01J 3/002 422/245.1 |
| 2006/0207497 A1 | 9/2006 | D'Evelyn et al. |
| 2006/0213429 A1 | 9/2006 | Motoki et al. |
| 2006/0214287 A1 | 9/2006 | Ogihara et al. |
| 2006/0255341 A1 | 11/2006 | Pinnington et al. |
| 2006/0255343 A1 | 11/2006 | Ogihara et al. |
| 2006/0288927 A1 | 12/2006 | Chodelka et al. |
| 2007/0057337 A1 | 3/2007 | Kano et al. |
| 2007/0096239 A1 | 5/2007 | Cao et al. |
| 2007/0105351 A1 | 5/2007 | Motoki et al. |
| 2007/0114569 A1 | 5/2007 | Wu et al. |
| 2007/0121690 A1 | 5/2007 | Fujii et al. |
| 2007/0131967 A1 | 6/2007 | Kawaguchi et al. |
| 2007/0141819 A1 | 6/2007 | Park et al. |
| 2007/0142204 A1 | 6/2007 | Park et al. |
| 2007/0151509 A1 | 7/2007 | Park et al. |
| 2007/0158785 A1 | 7/2007 | D'Evelyn et al. |
| 2007/0178039 A1 | 8/2007 | D'Evelyn et al. |
| 2007/0181056 A1 | 8/2007 | D'Evelyn et al. |
| 2007/0197004 A1 | 8/2007 | Dadgar et al. |
| 2007/0210074 A1 | 9/2007 | Maurer et al. |
| 2007/0215033 A1 | 9/2007 | Imaeda et al. |
| 2007/0215887 A1 | 9/2007 | D'Evelyn et al. |
| 2007/0218703 A1 | 9/2007 | Kaeding et al. |
| 2007/0228404 A1 | 10/2007 | Tran et al. |
| 2007/0252164 A1 | 11/2007 | Zhong et al. |
| 2007/0274359 A1 | 11/2007 | Takeuchi et al. |
| 2007/0290224 A1 | 12/2007 | Ogawa |
| 2008/0006831 A1 | 1/2008 | Ng |
| 2008/0023691 A1 | 1/2008 | Jang et al. |
| 2008/0025360 A1 | 1/2008 | Eichler et al. |
| 2008/0056984 A1 | 3/2008 | Yoshioka et al. |
| 2008/0073660 A1 | 3/2008 | Ohno et al. |
| 2008/0083741 A1 | 4/2008 | Giddings et al. |
| 2008/0083929 A1 | 4/2008 | Fan et al. |
| 2008/0083970 A1 | 4/2008 | Kamber et al. |
| 2008/0087919 A1 | 4/2008 | Tysoe et al. |
| 2008/0106212 A1 | 5/2008 | Yen et al. |
| 2008/0121906 A1 | 5/2008 | Yakushiji |
| 2008/0128752 A1 | 6/2008 | Wu |
| 2008/0156254 A1 | 7/2008 | Dwilinski et al. |
| 2008/0193363 A1 | 8/2008 | Tsuji |
| 2008/0198881 A1 | 8/2008 | Farrell et al. |
| 2008/0211416 A1 | 9/2008 | Negley et al. |
| 2008/0230765 A1 | 9/2008 | Yoon et al. |
| 2008/0272462 A1 | 11/2008 | Shimamoto et al. |
| 2008/0282978 A1 | 11/2008 | Butcher et al. |
| 2008/0285609 A1 | 11/2008 | Ohta et al. |
| 2008/0298409 A1 | 12/2008 | Yamashita et al. |
| 2009/0078955 A1 | 3/2009 | Fan et al. |
| 2009/0092536 A1 | 4/2009 | Kawabata et al. |
| 2009/0146170 A1 | 6/2009 | Zhong et al. |
| 2009/0218593 A1 | 9/2009 | Kamikawa et al. |
| 2009/0250686 A1 | 10/2009 | Sato et al. |
| 2009/0301387 A1 | 12/2009 | D'Evelyn |
| 2009/0301388 A1 | 12/2009 | D'Evelyn |
| 2009/0309105 A1 | 12/2009 | Letts et al. |
| 2009/0309110 A1 | 12/2009 | Raring et al. |
| 2009/0320745 A1 | 12/2009 | D'Evelyn et al. |
| 2010/0001300 A1 | 1/2010 | Raring et al. |
| 2010/0003492 A1 | 1/2010 | D'Evelyn |
| 2010/0003942 A1 | 1/2010 | Ikeda et al. |
| 2010/0025656 A1 | 2/2010 | Raring et al. |
| 2010/0031872 A1 | 2/2010 | D'Evelyn |
| 2010/0031873 A1 | 2/2010 | D'Evelyn |
| 2010/0031874 A1 | 2/2010 | D'Evelyn |
| 2010/0031875 A1 | 2/2010 | D'Evelyn |
| 2010/0031876 A1 | 2/2010 | D'Evelyn |
| 2010/0032691 A1 | 2/2010 | Kim |
| 2010/0075175 A1 | 3/2010 | Poblenz et al. |
| 2010/0104495 A1 | 4/2010 | Kawabata et al. |
| 2010/0108985 A1 | 5/2010 | Chung et al. |
| 2010/0109030 A1 | 5/2010 | Krames et al. |
| 2010/0109126 A1 | 5/2010 | Arena |
| 2010/0117101 A1 | 5/2010 | Kim et al. |
| 2010/0117118 A1 | 5/2010 | Dabiran et al. |
| 2010/0147210 A1 | 6/2010 | D'Evelyn |
| 2010/0151194 A1 | 6/2010 | D'Evelyn |
| 2010/0189981 A1 | 7/2010 | Poblenz et al. |
| 2010/0295088 A1 | 11/2010 | D'Evelyn et al. |
| 2011/0017298 A1 | 1/2011 | Lee |

(56) References Cited

U.S. PATENT DOCUMENTS

| | | |
|---|---|---|
| 2011/0062415 A1 | 3/2011 | Ohta et al. |
| 2011/0064103 A1 | 3/2011 | Ohta et al. |
| 2011/0100291 A1 | 5/2011 | D'Evelyn |
| 2011/0108081 A1 | 5/2011 | Werthen et al. |
| 2011/0121331 A1 | 5/2011 | Simonian et al. |
| 2011/0175200 A1 | 7/2011 | Yoshida |
| 2011/0183498 A1 | 7/2011 | D'Evelyn |
| 2011/0220912 A1 | 9/2011 | D'Evelyn |
| 2011/0256693 A1 | 10/2011 | D'Evelyn et al. |
| 2011/0262773 A1 | 10/2011 | Poblenz et al. |
| 2012/0000415 A1 | 1/2012 | D'Evelyn et al. |
| 2012/0007102 A1 | 1/2012 | Feezell et al. |
| 2012/0025231 A1 | 2/2012 | Krames et al. |
| 2012/0073494 A1 | 3/2012 | D'Evelyn |
| 2012/0091465 A1 | 4/2012 | Krames et al. |
| 2012/0118223 A1 | 5/2012 | D'Evelyn |
| 2012/0119218 A1 | 5/2012 | Su |
| 2012/0137966 A1 | 6/2012 | D'Evelyn et al. |
| 2012/0187412 A1 | 7/2012 | D'Evelyn et al. |
| 2012/0199952 A1 | 8/2012 | D'Evelyn et al. |
| 2013/0119401 A1 | 5/2013 | D'Evelyn et al. |
| 2013/0251615 A1 | 9/2013 | D'Evelyn et al. |
| 2013/0323490 A1 | 12/2013 | D'Evelyn et al. |
| 2014/0065360 A1 | 3/2014 | D'Evelyn et al. |

FOREIGN PATENT DOCUMENTS

| | | |
|---|---|---|
| WO | WO 2004/030061 | 4/2004 |
| WO | WO 2006/038467 | 4/2006 |
| WO | 2006/057463 | 6/2006 |
| WO | 2007/004495 | 1/2007 |
| WO | WO 2010/068916 | 6/2010 |
| WO | 2012/016033 | 2/2012 |

OTHER PUBLICATIONS

USPTO Office Action for U.S. Appl. No. 13/160,307 dated Jun. 26, 2014 (19 pages).
USPTO Office Action for U.S. Appl. No. 13/894,220 dated Jul. 31, 2014 (9 pages).
USPTO Office Action for U.S. Appl. No. 12/133,365 dated Feb. 20, 2014, 32 pages.
USPTO Office Action for U.S. Appl. No. 12/636,683 dated Feb. 24, 2014, 16 pages.
USPTO Office Action for U.S. Appl. No. 13/272,981 dated Mar. 13, 2014, 10 pages.
USPTO Notice of Allowance for U.S. Appl. No. 12/534,843 dated Jan. 24, 2013.
Communication from the Polish Patent Office re P394857 dated Jan. 22, 2013, 2 pages.
USPTO Notice of Allowance for U.S. Appl. No. 12/634,665 dated Feb. 15, 2013.
USPTO Office Action for U.S. Appl. No. 13/041,199 dated Mar. 12, 2013.
USPTO Notice of Allowance for U.S. Appl. No. 13/226,249 dated Feb. 21, 2013.
Altoukhov et al., 'High reflectivity airgap distributed Bragg reflectors realized by wet etching of AlInN sacrificial layers', Applied Physics Letters, vol. 95, 2009, pp. 191102-1-3.
Callahan et al., 'Synthesis and Growth of Gallium Nitride by the Chemical Vapor Reaction Process (CVRP)', MRS Internet Journal Nitride Semiconductor Research, vol. 4, No. 10, 1999, pp. 1-6.
Dorsaz et al., 'Selective oxidation of AlInN Layers for current confinement III-nitride devices', Applied Physics Letters, vol. 87, 2005, pp. 072102.
Ehrentraut et al., 'The ammonothermal crystal growth of gallium nitride—A technique on the up rise', Proceedings IEEE, 2010, 98(7), pp. 1316-1323.
Fang., 'Deep centers in semi-insulating Fe-doped native GaN substrates grown by hydride vapour phase epitaxy', Physica Status Solidi, vol. 5, No. 6, 2008, pp. 1508-1511.

Fujito et al., 'Development of bulk GaN crystals and nonpolar/semipolar substrates by HVPE', MRS Bulletin, 2009, 34, 5, pp. 313-317.
Gladkov et al., 'Effect of Fe doping on optical properties of freestanding semi-insulating HVPE GaN:Fe', Journal of Crystal Growth, 312, 2010, pp. 1205-1209.
Grzegory, 'High pressure growth of bulk GaN from Solutions in gallium', Journal of Physics Condensed Matter, vol. 13, 2001, pp. 6875-6892.
Moutanabbir, 'Bulk GaN Ion Cleaving', Journal of Electronic Materials, vol. 39, 2010, pp. 482-488.
Oshima et al., 'Thermal and Optical Properties of Bulk GaN Crystals Fabricated Through Hydride Vapor Phase Epitaxy With Void-Assisted Separation', Journal of Applied Physics, vol. 98, No. 10, 2005, pp. 103509-1-103509-4.
International Search Report of PCT Application No. PCT/US2009/067745, dated Feb. 5, 2010, 1 page total.
Porowski, 'High Resistivity GaN Single Crystalline Substrates', Acta Physica Polonica A, vol. 92, No. 2, 1997, pp. 958-962.
Porowski, 'Near Defect Free GaN Substrates', Journal of Nitride Semiconductor, 1999, pp. 1-11.
Sharma et al., 'Verticlaly oriented GaN-based air-gap distributed Bragg reflector structure fabricated using band-gap-selective photoelectrochemical etching', Applied Physics Letters, vol. 87, 2005, pp. 051107.
Tyagi et al., 'Partial Strain relaxation via misfit dislocation generation at heterointerfaces in (Al,In)GaN epitaxial layers grown on semipolar (1122) GaN free standing substrates', Applied Physics Letters 95, (2009) pp. 251905.
Wang et al., 'Ammonothermal Growth of GaN Crystals in Alkaline Solutions', Journal of Crystal Growth, vol. 287, 2006, pp. 376-380.
USPTO Office Action for U.S. Appl. No. 12/133,365 dated May 13, 2013.
USPTO Office Action for U.S. Appl. No. 12/497,969 dated May 16, 2013.
USPTO Office Action for U.S. Appl. No. 12/636,683 dated Jun. 12, 2013.
USPTO Office Action for U.S. Appl. No. 12/891,668 dated Jan. 10, 2013.
USPTO Notice of Allowance for U.S. Appl. No. 12/891,668 dated Mar. 20, 2013.
USPTO Notice of Allowance for U.S. Appl. No. 13/175,739 dated Mar. 21, 2013.
USPTO Office Action for U.S. Appl. No. 13/272,981 dated Mar. 20, 2013.
USPTO Office Action for U.S. Appl. No. 13/346,507 dated Dec. 21, 2012.
USPTO Notice of Allowance for U.S. Appl. No. 13/346,507 dated Apr. 22, 2013.
USPTO Notice of Allowance for U.S. Appl. No. 13/548,931 dated Jun. 3, 2013.
Copel et al., 'Surfactants in Epitaxial Growth', Physical Review Letters, Aug. 7, 1989, vol. 63, No. 6, p. 632-635.
Lu et al., 'Structure of the Cl-passivated GaAs(111) surface', Physical Review B, Nov. 15, 1998, vol. 58, No. 20, pp. 13820-13823.
Massies et al., 'Surfactant mediated epitaxial growth of InxGa1—xAs on GaAs (001)', Applied Physics Letters, vol. 61, No. 1, Jul. 6, 1992, pp. 99-101.
Sumiya et al., 'High-pressure synthesis of high-purity diamond crystal', Diamond and Related Materials, 1996, vol. 5, pp. 1359-1365.
Communication from the Chinese Patent Office re 200980134876.2 dated Jul. 3, 2013, 14 pages.
Communication from the Polish Patent Office re P394857 dated Aug. 14, 2013, 2 pages.
USPTO Office Action for U.S. Appl. No. 12/133,365 dated Aug. 21, 2013, 29 pages.
USPTO Office Action for U.S. Appl. No. 12/334,418 dated Sep. 17, 2013, 27 pages.
USPTO Office Action for U.S. Appl. No. 12/497,969 dated Sep. 6, 2013, 21 pages.

(56) References Cited

OTHER PUBLICATIONS

USPTO Office Action for U.S. Appl. No. 12/636,683 dated Aug. 16, 2013, 16 pages.
USPTO Office Action for U.S. Appl. No. 12/697,171 dated Jun. 20, 2013, 17 pages.
USPTO Office Action for U.S. Appl. No. 12/697,171 dated Aug. 20, 2013, 17 pages.
USPTO Office Action for U.S. Appl. No. 13/272,981 dated Aug. 15, 2013, 13 pages.
USPTO Office Action for U.S. Appl. No. 13/472,356 dated Dec. 9, 2013 (11 pages).
Choi et al., '2.51 microcavity InGaN light-emitting diodes fabricated by a selective dry-etch thinning process', Applied Physics Letters, 2007, 91(6), 061120.
D'Evelyn et al., 'Bulk GaN Crystal Growth by the High-Pressure Ammonothermal Method,' Journal of Crystal Growth, vol. 300, 2007, pp. 11-16.
Fukuda et al., 'Prospects for the Ammonothermal Growth of Large GaN Crystal,' Journal of Crystal Growth, vol. 305, 2007, pp. 304-310.
Iso et al., 'High Brightness Blue InGaN/GaN Light Emitting Diode on Nonpolar m-Plane Bulk GaN Substrate,' Japanese Journal of Applied Physics, 2007, vol. 46, No. 40, pp. L960-L962.
Lide et al., 'Thermal Conductivity of Ceramics and Other Insulating Materials,' CRC Handbook of Chemistry and Physics, 91st Edition, 2010-2011, pp. 12-203 and 12-204.
http://www.matbase.com/material/non-ferrous-metals/other/molybdenum/properties, Data Table for: Non-Ferrous Metals: Other Metals: Molybdenum, Mar. 28, 2011, pp. 1.
Pattison et al., 'Gallium Nitride Based Microcavity Light Emitting Diodes With 2λ, Effective Cavity Thickness', Applied Physics Letters, vol. 90, Issue 3, 031111 (2007) 3pg.
Sarva et al., 'Dynamic Compressive Strength of Silicon Carbide Under Uniaxial Compression,' Material Sciences and Engineering, vol. A317, 2001, pp. 140-144.
Tyagi et al., 'Semipolar (1011) InGaN/GaN Laser Diodes on Bulk GaN Substrates,' Japanese Journal of Applied Physics, vol. 46, No. 19, 2007, pp. L444-L445.
Weisbuch et al., 'Recent results and latest views on microcavity LEDs', Light-Emitting Diodes: Research, Manufacturing, and Applications VIII, ed. By S.A. Stockman et al., Proc. SPIE, vol. 5366, p. 1-19 (2004).
USPTO Office Action for U.S. Appl. No. 12/133,364 dated Nov. 26, 2010.
USPTO Office Action for U.S. Appl. No. 12/133,364 dated Jun. 1, 2011.
USPTO Notice of Allowance for U.S. Appl. No. 12/133,364 dated Oct. 11, 2011.
USPTO Office Action for U.S. Appl. No. 12/133,365 dated Jun. 9, 2011.
USPTO Office Action for U.S. Appl. No. 12/133,365 dated Oct. 18, 2011.
USPTO Office Action for U.S. Appl. No. 12/334,418 dated Apr. 5, 2011.
USPTO Office Action for U.S. Appl. No. 12/334,418 dated Oct. 19, 2011.
USPTO Office Action for U.S. Appl. No. 12/478,736 dated Sep. 27, 2011.
USPTO Office Action for U.S. Appl. No. 12/478,736 dated Feb. 7, 2012.
USPTO Notice of Allowance for U.S. Appl. No. 12/478,736 dated Apr. 23, 2012.
USPTO Notice of Allowance for U.S. Appl. No. 12/478,736 dated Oct. 9, 2012.
USPTO Office Action for U.S. Appl. No. 12/484,095 dated Nov. 10, 2010.
USPTO Office Action for U.S. Appl. No. 12/484,095 dated Jul. 8, 2011.
USPTO Office Action for U.S. Appl. No. 12/497,969 dated Feb. 2, 2012.
USPTO Office Action for U.S. Appl. No. 12/497,969 dated Jul. 5, 2012.
USPTO Office Action for U.S. Appl. No. 12/534,838 dated May 3, 2011.
USPTO Office Action for U.S. Appl. No. 12/534,838 dated Jan. 13, 2012.
USPTO Office Action for U.S. Appl. No. 12/534,838 dated Mar. 20, 2012.
USPTO Notice of Allowance for U.S. Appl. No. 12/534,838 dated Jun. 8, 2012.
USPTO Office Action for U.S. Appl. No. 12/534,843 dated Sep. 10, 2012.
USPTO Office Action for U.S. Appl. No. 12/534,844 dated Sep. 16, 2010.
USPTO Office Action for U.S. Appl. No. 12/534,844 dated Feb. 4, 2011.
USPTO Notice of Allowance for U.S. Appl. No. 12/534,849 dated Jul. 31, 2012.
USPTO Office Action for U.S. Appl. No. 12/534,857 dated Sep. 1, 2010.
USPTO Notice of Allowance for U.S. Appl. No. 12/534,857 dated May 27, 2011.
USPTO Office Action for U.S. Appl. No. 12/546,458 dated Jul. 20, 2011.
USPTO Notice of Allowance for U.S. Appl. No. 12/546,458 dated Nov. 28, 2011.
USPTO Office Action for U.S. Appl. No. 12/556,558 dated Sep. 16, 2010.
USPTO Notice of Allowance for U.S. Appl. No. 12/556,558 dated Mar. 22, 2011.
USPTO Office Action for U.S. Appl. No. 12/556,562 dated Sep. 15, 2010.
USPTO Office Action for U.S. Appl. No. 12/556,562 dated Mar. 21, 2011.
USPTO Notice of Allowance for U.S. Appl. No. 12/556,562 dated Jul. 27, 2011.
USPTO Office Action for U.S. Appl. No. 12/569,337 dated May 9, 2012.
USPTO Notice of Allowance for U.S. Appl. No. 12/569,337 dated Nov. 15, 2012.
USPTO Office Action for U.S. Appl. No. 12/569,841 dated Dec. 23, 2011.
USPTO Office Action for U.S. Appl. No. 12/569,844 dated Oct. 12, 2012.
USPTO Office Action for U.S. Appl. No. 12/634,665 dated Apr. 25, 2012.
USPTO Office Action for U.S. Appl. No. 12/634,665 dated Oct. 1, 2012.
USPTO Office Action for U.S. Appl. No. 12/724,983 dated Mar. 5, 2012.
USPTO Notice of Allowance for U.S. Appl. No. 12/754,886 dated May 17, 2012.
USPTO Notice of Allowance for U.S. Appl. No. 12/754,886 dated Jun. 5, 2012.
USPTO Notice of Allowance for U.S. Appl. No. 12/754,886 dated Jun. 20, 2012.
USPTO Office Action for U.S. Appl. No. 12/785,404 dated Mar. 6, 2012.
USPTO Notice of Allowance for U.S. Appl. No. 12/785,404 dated Jul. 16, 2012.
USPTO Office Action for U.S. Appl. No. 12/891,668 dated Sep. 25, 2012.
USPTO Office Action for U.S. Appl. No. 13/025,833 dated Jul. 12, 2012.
USPTO Office Action for U.S. Appl. No. 13/041,199 dated Nov. 30, 2012.
USPTO Office Action for U.S. Appl. No. 13/175,739 dated Dec. 7, 2012.
USPTO Office Action for U.S. Appl. No. 13/179,346 dated Aug. 17, 2012.
USPTO Office Action for U.S. Appl. No. 13/179,346 dated Dec. 13, 2012.

(56) References Cited

OTHER PUBLICATIONS

USPTO Office Action for U.S. Appl. No. 13/226,249 dated Oct. 10, 2012.
USPTO Notice of Allowance for U.S. Appl. No. 13/425,304 dated Aug. 22, 2012.

* cited by examiner

CAPSULE FOR HIGH PRESSURE, HIGH TEMPERATURE PROCESSING OF MATERIALS AND METHODS OF USE

The present application claims the benefit of priority to U.S. Provisional Application No. 61/550,794 filed on Oct. 24, 2011, which is incorporated by reference in entirety.

BACKGROUND OF THE DISCLOSURE

The disclosure relates generally to a capsule to be used in high pressure, high temperature applications. The disclosure relates generally to a capsule to be used with a high pressure apparatus. More particularly, the disclosure relates to a capsule used in conjunction with a high-pressure apparatus for processing materials in a supercritical fluid. Supercritical fluids may be used to process a wide variety of materials. Examples of supercritical fluids applications include extractions in supercritical carbon dioxide, the growth of quartz crystals in supercritical water, and the synthesis of a variety of nitrides in supercritical ammonia.

Processes that employ supercritical fluids are commonly performed at high pressure and high temperature within a pressure vessel. Most conventional pressure vessels not only provide a source of mechanical support for the pressure applied to reactant materials and supercritical fluids, but also serve as a container for the supercritical fluid and material being processed. The processing limitations for such pressure vessels are typically limited to a maximum temperature in the range between about 400° C. and 600° C. and a maximum pressure in the range between about 0.1 Giga-Pascals (also referred as "GPa") and 0.5 GPa.

Processing material with supercritical fluids often requires a container or capsule that is substantially both chemically inert and impermeable to the solvent and any gases that might be generated by the process. The capsule should also be substantially impermeable to any gases or materials on the outside of the capsule. These capsules are commonly made in the form of cylinders, possessing a wall and two ends disposed opposite each other along the axis of the cylinder. In one approach, the material to be processed, along with a solvent (liquid) that forms a supercritical fluid at elevated temperatures, is introduced into a capsule at low temperature. After the capsule has been sealed and returned to near room temperature, the capsule will possess an elevated internal pressure as dictated by the vapor pressure and temperature of the solvent (liquid) within the capsule. In the case of ammonia at room temperature, the pressure within the capsule is approximately 150 pounds per square inch. This internal pressure can cause deformation, strain, cracks, leaks, and failure of the capsule, particularly for capsules larger than several inches in dimension, and/or when the capsule is fabricated from a soft metal such as silver or gold.

Some legacy approaches use a capsule, principally of fused silica or quartz or glass, placed in contact with a pressure medium, which is within an outer capsule. This capsule within a capsule is designed to use the pressure medium between the two capsules to either counterbalance the pressure from the inner capsule or to provide an overpressure so that the inner capsule is under a compressive or neutral stress, rather than under tension, since the materials of construction of the inner capsule (fused silica, quartz or other glass) tend to fail when under tension. The outer capsule, therefore, is the principle pressure vessel and must be able to withstand the longitudinal and radial stresses as dictated by the fluid and its temperature inside. Depending on the capsule material and the intended volumetric capacity of the capsule, this may require very thick capsule walls and ends, which may be limiting, especially on a manufacturing scale and for materials such as silver, gold, or platinum. Other approaches use reinforcement members attached to the ends of the capsule. Such reinforcement members attached to the ends of the capsule often do not prevent failure of the capsule due to radial forces on the body (e.g., walls) of the capsule, and they do not reinforce against longitudinal forces that act to elongate the capsule, both of which are significant for capsules of large dimension.

From the above, it is seen that improved techniques for processing materials in a high pressure apparatus are highly desirable.

BRIEF SUMMARY OF THE DISCLOSURE

The present disclosure relates generally to a capsule to be used in high pressure, high temperature applications. The disclosure relates generally to a capsule to be used with a high pressure apparatus. More particularly, the disclosure relates to a capsule used in conjunction with a high-pressure apparatus for processing at least one material in a supercritical fluid. The disclosure provides a process capsule that receives structural support from a support capsule, and methods of use for this capsule, one method including processing a material in a supercritical fluid. The disclosure also provides a process capsule that receives structural support from a support sleeve, and methods of use for this capsule, including processing a material in a supercritical fluid.

In a specific embodiment, the disclosure provides a method for processing a material in a supercritical fluid, e.g., gallium nitride (GaN) in ammonia. In one embodiment, the method includes loading at least one material (e.g., GaN) into an interior volume of a process capsule through a first open end. The process capsule has a first closed end and the first open end. The method includes attaching a first capsule end onto the first open end of the process capsule and loading the process capsule into an interior volume of a support capsule, which has a second closed end and a second open end. A second support capsule end is attached to the second open end of the support capsule. The interior volume of the process capsule is filled with at least a solvent or fluid, and the process capsule is sealed. After placing the process capsule within a support capsule in a high pressure apparatus, the capsule is heated to generate a supercritical fluid within the process capsule causing formation of a crystalline material, e.g., III-nitride, including GaN, AlN, InN, or an alloy. After the process is complete the material is removed from the process capsule.

Sealing the process capsule is performed using a conventional process, e.g., welding, tungsten inert gas (TIG) welding, orbital welding, arc welding, e-beam welding, ultrasonic welding, magnetic pulse welding, torch welding, vibratory welding, pinch sealing, brazing, cold welding, among other techniques. In one embodiment, a material is disposed between the process capsule and the support capsule. One or more other elements, compounds, materials, or chemical additives may be disposed between the process capsule and the support capsule, including but not limited to steel, stainless steel, carbon steel, nickel, nickel-based alloy, Inconel® nickel-chromium and iron alloy, Hastelloy® nickel-molybdenum-chromium alloy, René® 41 nickel-based alloy, Waspalloy® nickel-based alloy, Mar-M 247® polycrystalline cast nickel-based alloy, Monel® nickel-copper alloy, Stellite® cobalt-chromium alloy, copper, copper-based alloy, zirconium, niobium, molybdenum, molybdenum disulfide, tantalum, tungsten, rhenium, platinum, platinum-based alloy, palladium, iridium, ruthenium, rhodium, rhenium, osmium, sulfur, tantalum, titanium, vanadium, chromium, iron, iron-based alloy, gold, silver, $MC_x^- N_yO_z$, wherein M is at least one of aluminum, boron silicon, titanium, vanadium, chromium, yttrium, zirconium, lanthanum, a rare earth metal, hafnium, tantalum, tungsten, and wherein each of x, y, and z is between 0 and 3 (i.e., 0<x, y, z<3), aluminum, graphite, graphite foil, salt, boron nitride, anti-seize lubricant, beryllium, magnesium, calcium, strontium, barium, lithium, sodium, potassium, rubidium, cesium, combinations thereof, and the like. In a specific embodiment, the support capsule comprises steel, stainless steel, carbon steel, nickel, nickel-based alloy, Inconel® nickel-chromium and iron alloy, Hastelloy® nickel-molybdenum-chromium alloy, René® 41 nickel-based alloy, Waspalloy® nickel-based alloy, Mar-M 247® polycrystalline cast nickel-based alloy, Monel® nickel-copper alloy, Stellite® cobalt-chromium alloy, copper, copper-based alloy, zirconium, niobium, molybdenum, tantalum, tungsten, rhenium, platinum, platinum-based alloy, palladium, iridium, ruthenium, rhodium, osmium, titanium, vanadium, chromium, iron, iron-based alloy, gold, silver, or aluminum, combinations thereof, and the like. In one embodiment, the method also includes providing a fluid disposed between the process capsule and the support capsule. In a specific embodiment, the method includes providing a fluid disposed between the support capsule and the high pressure apparatus. In certain embodiments, the fluid disposed between the process capsule and the support capsule and/or the support capsule and the high pressure apparatus comprises air, oxygen, hydrogen, ammonia, argon, water, nitrogen, helium, nitrous oxide, carbon dioxide, methane, ethane, propane, ethylene, propylene, methanol, isopropanol, acetic acid, benzene, toluene, ethanol, or acetone, combinations of these, among others. In one embodiment, the space between the process capsule and the support capsule and/or the space between support capsule and the high pressure apparatus is evacuated.

In a specific embodiment, the disclosure provides a capsule for processing a material in a supercritical fluid. The capsule includes a process capsule comprised of a closed end, which is characterized by a first Young's modulus and a first yield strength, a process capsule wall, which is characterized by a second Young's modulus and a second yield strength. The capsule also has a sealed end, which is characterized by a third Young's modulus and a third yield strength. The closed end, the wall, and the sealed end are configured to define an internal volume capable of receiving at least a material and a solvent. The capsule also has a support capsule comprised of a closed support end, which is characterized by a fourth Young's modulus and a fourth yield strength, a support capsule wall, which is characterized by a fifth Young's modulus and a fifth yield strength, and a sealed support end, which is characterized by a sixth Young's modulus and a sixth yield strength. In certain embodiments, the closed support end, support capsule wall, and sealed support end are configured to receive a process capsule. The capsule is also configured such that the process capsule is disposed within the support capsule. In one embodiment, the yield strengths of the closed support end, the support capsule wall, and the sealed support end exceed the yield strengths of the process capsule closed end, wall, and sealed end.

In one embodiment of the present disclosure, the capsule includes a wall having a first end and a second end and a length, a closed end disposed at the first end, a sealed end (or sealable end) disposed at the second end, and a support sleeve disposed on at least the wall. In certain embodiments, the support sleeve is configured to provide mechanical support for the capsule. The capsule may also have a support sleeve disposed on at least the wall, closed end, or sealed end, which is configured to provide mechanical support for the capsule. In certain embodiments, the support sleeve is characterized by a material thickness and a first Young's modulus and a first yield strength and configured to provide mechanical support for the capsule. A fluid and one or materials may be disposed within the capsule to process a material in a supercritical fluid.

The present disclosure provides a number of advantages over prior approaches. For example, in one embodiment, the process capsule wall is radially reinforced, enabling the capsule to be pressurized without the capsule substantially yielding or bowing, possibly resulting in capsule failure, and without requiring exorbitantly thick and expensive capsule materials. This radial reinforcement improves capsule robustness. In another embodiment, a process capsule is disposed within a support capsule that provides structural support for the process capsule, enabling the process capsule to be pressurized without significant yielding or bowing, possibly resulting in capsule failure, and without requiring exorbitantly thick and expensive capsule materials. According to the present disclosure, the capsule may be formed from capsule components (i.e., closed end, sealed end, wall, support capsule wall, closed support end, sealed support end) using a butt joint by orbital welding. Furthermore, the present disclosure also discloses capsule designs that do not incorporate a fill tube. Fill tubes may be a source of leaks in high pressure processes.

DETAILED DESCRIPTION OF THE DISCLOSURE

In the following description reference is made to a capsule that is suitable for use in high pressure and high temperature applications, and the capsule may be used for processing supercritical fluids or materials within supercritical fluids. The capsule may be disposed within a high-pressure apparatus for processing materials in a supercritical fluid, e.g., processing or growing gallium nitride in a supercritical fluid. Merely by way of example, the disclosure may be applied to growing crystals of GaN, AlN, InN, InGaN, AlGaN, AlInGaN, and others for manufacture of bulk or patterned substrates. Such bulk or patterned substrates can be used for a variety of applications including optoelectronic devices, lasers, light emitting diodes, solar cells, photodetectors, and integrated circuits, transistor devices, other device structures, photoelectrochemical water splitting and hydrogen generation, and others. In the following description, terms such as "top", "bottom", "up", "upward", "down", "downward", "outward", "inward", among others are used and are words convenience and are not to be construed as limiting terms.

The present disclosure provides capsule designs suitable for use in high pressure and high temperature applications. The designs are capable of processing materials at pressures and temperatures of up to approximately 8 GPa and 1500° C., respectively. One aspect of the present disclosure provides a capsule suitable for use in high pressure and high temperature applications where the capsule wall is radially reinforced by a capsule sleeve. The radially reinforced capsule wall enables the capsule to be pressurized without substantial yielding, bowing, or failure of the capsule, and without requiring exorbitantly thick and expensive capsule materials. In the following description reference is made to this capsule with a capsule sleeve as a "capsule", "capsule with a sleeve", "capsule with a capsule support sleeve", "capsule with a capsule sleeve", "capsule with a support capsule sleeve", among others, and it should be understood that these are terms of convenience and may be used interchangeably and should not be construed as limiting terms. In another aspect of the present disclosure, a dual capsule design is described in which a process capsule is disposed within a support capsule that provides structural support for the process capsule. In the following description reference is made to this process capsule disposed within a support capsule as a "capsule" or "dual capsule" and it should be understood that these are terms of convenience and should not be construed as limiting terms.

Figure 1:
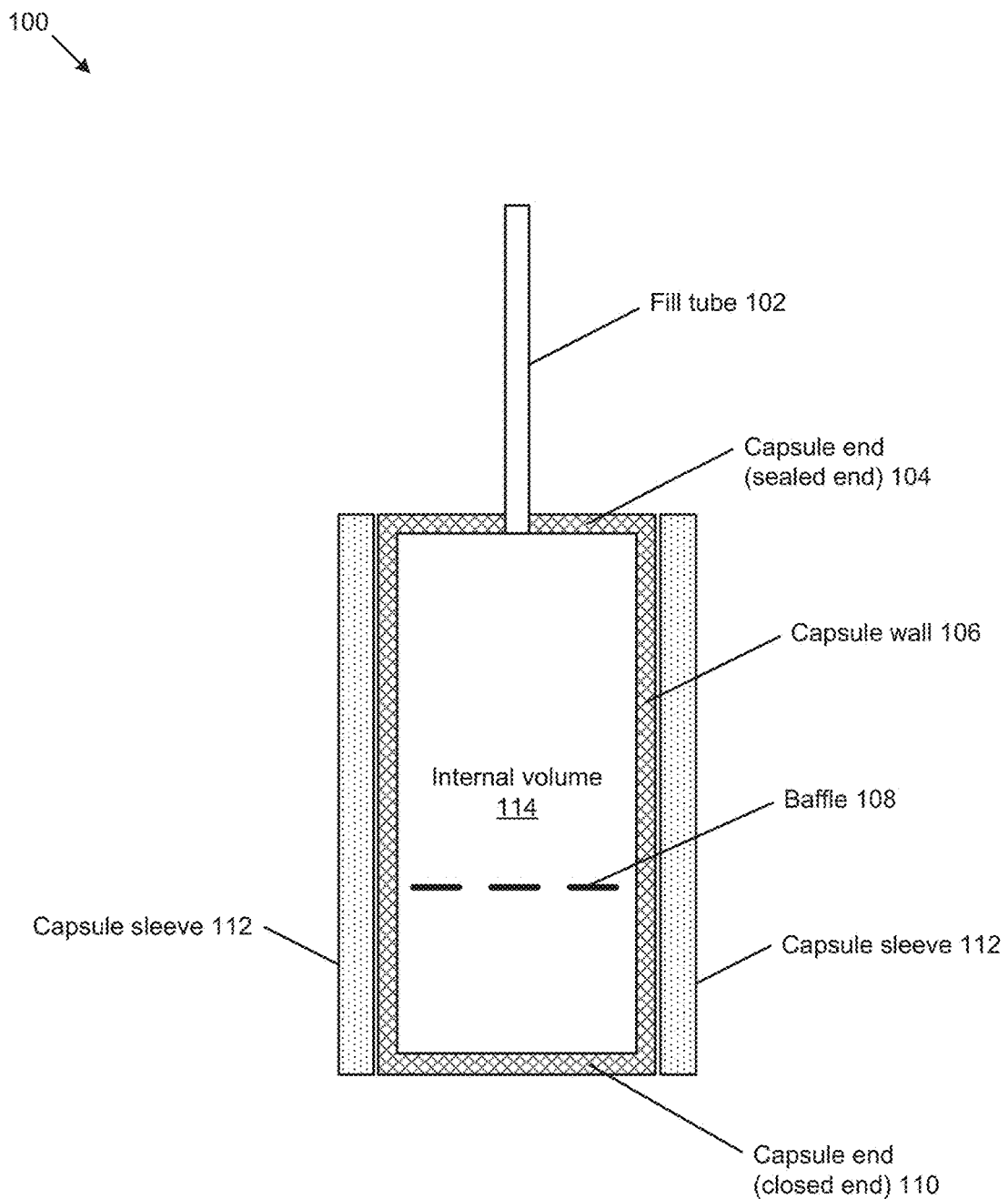
FIG. 1 is a diagram showing a capsule which contains a support sleeve, according to some embodiments.

FIG. 1 is a schematic 100 showing a capsule, which includes a support sleeve. The support sleeve is configured to provide radial support for the capsule. The capsule possesses a closed end 110, at least one wall adjoining the closed end 110 and extending therefrom, and a sealed end 104 adjoining the at least one wall and opposite of the closed end. "Closed end", "wall", and "sealed end" are terms of convenience and should not be considered to be limiting terms. The closed end 110, at least one wall, and the sealed end 104 define an internal volume 114 within the capsule capable of containing at least one material and at least one solvent that becomes a supercritical fluid at a high temperature and high pressure condition (also referred to as "HPHT"). HPHT conditions encompass temperatures greater than about room temperature (about 20° C.) and pressures greater than about 1 atmosphere. In one embodiment, the capsule possesses a cylindrical member or shape. Capsule 100 may also be provided with at least one baffle 108 within internal volume 114, the one or more baffles 108 serving to create separate regions within the internal volume 114. The separate regions are in fluid communication with each other since the one or more baffles 108 will typically have a cross-sectional area smaller than the area defined by the inner diameter of the capsule, thereby producing a fractional open area of the baffle. In a specific embodiment, baffle 108 has a fractional open area of between about 0.5% and about 60%, but can also have other percentages. The baffle material may comprise copper, copper-based alloy, gold, silver, palladium, platinum, platinum-based alloy, iridium, ruthenium, rhodium, osmium, titanium, vanadium, chromium, chromium-based alloy, iron, iron-based alloy, nickel, nickel-based alloy, zirconium, niobium, molybdenum, tantalum, tungsten, rhenium, silica, alumina, combinations of any of the foregoing, and the like.

In one embodiment, the capsule is substantially chemically inert and impermeable with respect to the at least one material, solvent, and supercritical fluid formed by the solvent disposed within the capsule. In certain embodiments, the capsule is impermeable to at least one of hydrogen, oxygen, and nitrogen. The closed end, at least one wall, and sealable end each have a thickness between about 0.1 mm and about 100 mm according to a specific embodiment. Other thicknesses can also be used depending upon the specific embodiment.

The capsule possesses an outer sleeve around at least a wall of the capsule, the closed end 110, or the sealed end. The capsule sleeve 112 serves to provide mechanical support for the capsule. The capsule sleeve 112 provides radial support for the capsule. The capsule sleeve may be mechanically coupled to the wall of the capsule or slidably inserted over the capsule. In one embodiment, the capsule sleeve 112 is constructed to have a yield strength which, when taken in combination with the yield strength of the capsule wall 106, exceeds that of the hoop stress exerted on the capsule by the vapor pressure and temperature of a fluid (or solvent) disposed within the capsule. In one embodiment, the capsule sleeve 112 has a yield strength that exceeds that of the hoop stress exerted on the capsule by the vapor pressure and temperature of a fluid (or solvent) disposed within the capsule. In one embodiment, the capsule sleeve is formed from one or more materials with a higher Young's modulus than the Young's modulus of a material of the capsule. In one embodiment, the capsule sleeve is formed from a material with a higher yield strength than the yield strength of the capsule material. The capsule may comprise copper, copper-based alloy, gold, silver, palladium, platinum, platinum-based alloy, iridium, ruthenium, rhodium, osmium, titanium, vanadium, chromium, chromium-based alloy, iron, iron-based alloy, nickel, nickel-based alloy, zirconium, niobium, molybdenum, tantalum, tungsten, rhenium, combinations of any of the foregoing, and the like. In certain embodiments of the present disclosure, the capsule is constructed of a deformable material that enables the capsule to expand when pressurized by the at least one solvent within the capsule. The capsule sleeve may comprise steel, stainless steel, carbon steel, nickel, nickel-based alloy, Inconel® nickel-chromium and iron alloy, Hastelloy® nickel-molybdenum-chromium alloy, René® 41 nickel-based alloy, Waspalloy® nickel-based alloy, Mar-M 247® polycrystalline cast nickel-based alloy, Monel® nickel-copper alloy, Stellite® cobalt-chromium alloy, copper, copper-based alloy, zirconium, niobium, molybdenum, tantalum, tungsten, rhenium, platinum, platinum-based alloy, palladium, iridium, ruthenium, rhodium, osmium, titanium, vanadium, chromium, chromium-based alloy, iron, iron-based alloy, gold, silver, or aluminum, combinations of any of the foregoing, and the like. The capsule sleeve may have a thickness greater than 0.001 inches, greater than 0.010 inches, greater than 0.100 inches, greater than 0.250 inches, greater than 0.5 inches, greater than 1 inches, greater than 2 inches, or greater than 5 inches.

The capsule sleeve may be constructed and applied in multiple ways. The capsule may be supported by multiple capsule sleeves that collectively may be referred to as a "capsule sleeve". The capsule sleeve may be constructed from a single tube, rolled and welded from sheet material, or composed of multiple segments to form a capsule sleeve that may provide radial support. The multiple segments may be stacked vertically and/or radially to provide structural support. Multiple capsule sleeves may be radially arranged to surround any or all portions of the capsule. Multiple capsule sleeve components may be brazed, welded, glued, cemented, interference fit (also referred to as press fit or friction fit), or otherwise bonded together to form the capsule sleeve. The capsule sleeve may cover any fraction of the capsule wall 106, but is can be over the entire wall of the capsule, and may extend over the ends (sealed end and closed end). The capsule sleeve may be brazed, welded, glued, interference fit or otherwise bonded to the capsule. The braze alloy may comprise at least one of copper, silver, gold, nickel, or palladium. The braze may be applied as a foil with a thickness between 0.001 inch and 0.025 inch and the bond may be effected by heating the capsule/braze/capsule sleeve above the liquidus temperature of the braze alloy under a suitable atmosphere, such as argon, argon/hydrogen, or hydrogen. In one embodiment, a material may be placed between the capsule and the capsule sleeve. Materials placed between the capsule and the sleeve may comprise nickel, rhodium, platinum, palladium, iridium, ruthenium, rhenium, tungsten, molybdenum, molybdenum disulfide, niobium, silver, sulfur, iridium, tantalum, $MC_xN_yO_z$, wherein M is at least one of aluminum, boron silicon, titanium, vanadium, chromium, yttrium, zirconium, lanthanum, a rare earth metal, hafnium, tantalum, tungsten, and wherein each of x, y, and z is between 0 and 3 (i.e., 0<x, y, z<3), graphite, graphite foil, titanium, salt, boron nitride, anti-seize lubricant, and combinations of any of the foregoing. The space between the capsule and the capsule sleeve also may be filled with a solvent or fluid such as air, oxygen, hydrogen, ammonia, argon, water, nitrogen, helium, nitrous oxide, carbon dioxide, methane, ethane, propane, ethylene, propylene, methanol, isopropanol, acetic acid, benzene, toluene, ethanol, acetone, a combination of any of the foregoing, and the like. The space between the capsule and the capsule sleeve may be evacuated.

Figure 7:
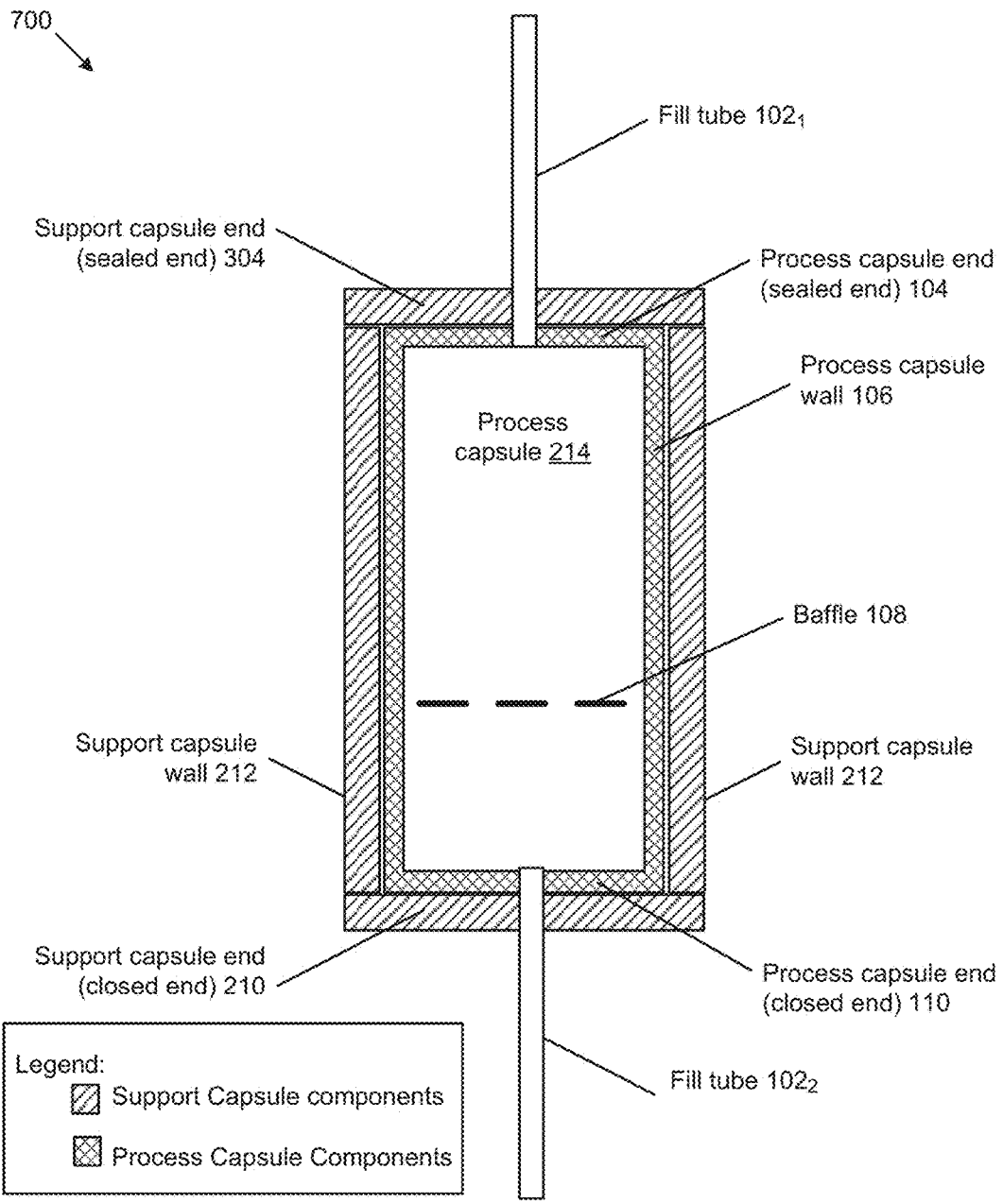
FIG. 7 is a diagram of a capsule with configurations of fill tubes, according to various embodiments.

In a specific embodiment, as shown in FIG. 1, the capsule has at least one fill tube 102 disposed on a portion of the capsule sealed end. In a specific embodiment, the fill tube 102 has an opening operably coupled to the interior region of the capsule. In a specific embodiment, as shown in FIG. 7, the capsule has at least one fill tube $102_2$ disposed on a portion of the capsule closed end. In a specific embodiment, as shown in FIG. 7, the capsule has at least one fill tube $102_1$ disposed on a portion of the capsule sealed end and the capsule has at least one fill tube $102_2$ disposed on a portion of the capsule closed end.

According to the present disclosure, the capsule with the support capsule sleeve will usually be placed in a pressure apparatus (high pressure apparatus), such as an autoclave, "zero-stroke" pressure apparatus, or a pressure apparatus with stroke. In one embodiment, the capsule is placed in the high pressure apparatus without the support sleeve. This may be accomplished, for example, by placing the capsule sleeve in contact with a restraint piece on the high pressure apparatus, thereby restraining the capsule sleeve, and then moving the capsule into the high pressure apparatus. This enables the capsule to be placed into the high pressure apparatus without significant deformation of the capsule or capsule failure and without the additional capsule sleeve. Other materials may be placed between the capsule (which may or may not include the capsule sleeve) and the pressure apparatus including nickel, rhodium, platinum, palladium, iridium, ruthenium, rhenium, tungsten, molybdenum, molybdenum disulfide, niobium, silver, sulfur, iridium, tantalum, $MC_xN_yO_z$, wherein M is at least one of aluminum, boron silicon, titanium, vanadium, chromium, yttrium, zirconium, lanthanum, a rare earth metal, hafnium, tantalum, tungsten, and wherein each of x, y, and z is between 0 and 3 (i.e., 0<x, y, z<3), graphite, graphite foil, titanium, salt, boron nitride, anti-seize lubricant, and combinations thereof. The space between the capsule and the pressure apparatus may be filled with a solvent or fluid such as but not limited to air, oxygen, hydrogen, ammonia, argon, water, nitrogen, helium, nitrous oxide, carbon dioxide, methane, ethane, propane, ethylene, propylene, methanol, isopropanol, acetic acid, benzene, toluene, ethanol, acetone, a combination of any of the foregoing, and the like. The space between the capsule and the pressure apparatus may be evacuated.

Techniques for processing materials in supercritical fluids within a capsule with a support capsule sleeve can be described in terms of method steps as described briefly in the following paragraphs (also see FIG. 8): Load at least one material into the interior volume of the capsule, which has a closed end and a sealed end; Place a support sleeve around the capsule; Fill the interior volume of the capsule with solvent; Seal the capsule; Place the capsule in a high pressure apparatus; Heat the capsule to generate a supercritical fluid; Cool the capsule; Remove material from the capsule; and Perform other steps as desired.

The above sequence of steps provides a method according to an embodiment of the disclosure. Other alternatives can also be provided where steps are added, one or more steps are removed, or one or more steps are provided in a different sequence. For example, in the above sequence of steps, the support sleeve may be placed around the capsule after filling the interior volume of the capsule with a solvent. In this embodiment, it is preferable to maintain the solvent at a low temperature, such as below room temperature, for the time between filling the capsule with a solvent and application of the sleeve. This reduces the vapor pressure of the solvent so that the capsule does not substantially deform and possibly catastrophically fail. The sequence of steps just described is as follows: Load at least one material into the interior volume of the capsule, which has a closed end and a sealed end; Fill the interior volume of the capsule with solvent; Seal the capsule; Place a support sleeve around the capsule; Place the capsule in a high pressure apparatus; Heat the capsule to generate a supercritical fluid; Cool the capsule; Remove material from the capsule; and Perform other steps as desired.

The above sequence of steps provides a method according to an embodiment of the disclosure. Other alternatives can also be provided where steps are added, one or more steps are removed, or one or more steps are provided in a different sequence. For example, in the above sequence of steps, the support sleeve may be placed around the capsule prior to sealing the capsule. This procedure is as follows: Load at least one material into the interior volume of the capsule, which has a closed end and a sealed end; Fill the interior volume of the capsule with solvent; Place a support sleeve around the capsule; Seal the capsule; Place the capsule in a high pressure apparatus; Heat the capsule to generate a supercritical fluid; Cool the capsule; Remove material from the capsule; and Perform other steps as desired. This sequence of steps provides a method according to an embodiment of the disclosure. Other alternatives can also be provided where steps are added, one or more steps are removed, or one or more steps are provided in a different sequence.

Figure 2:
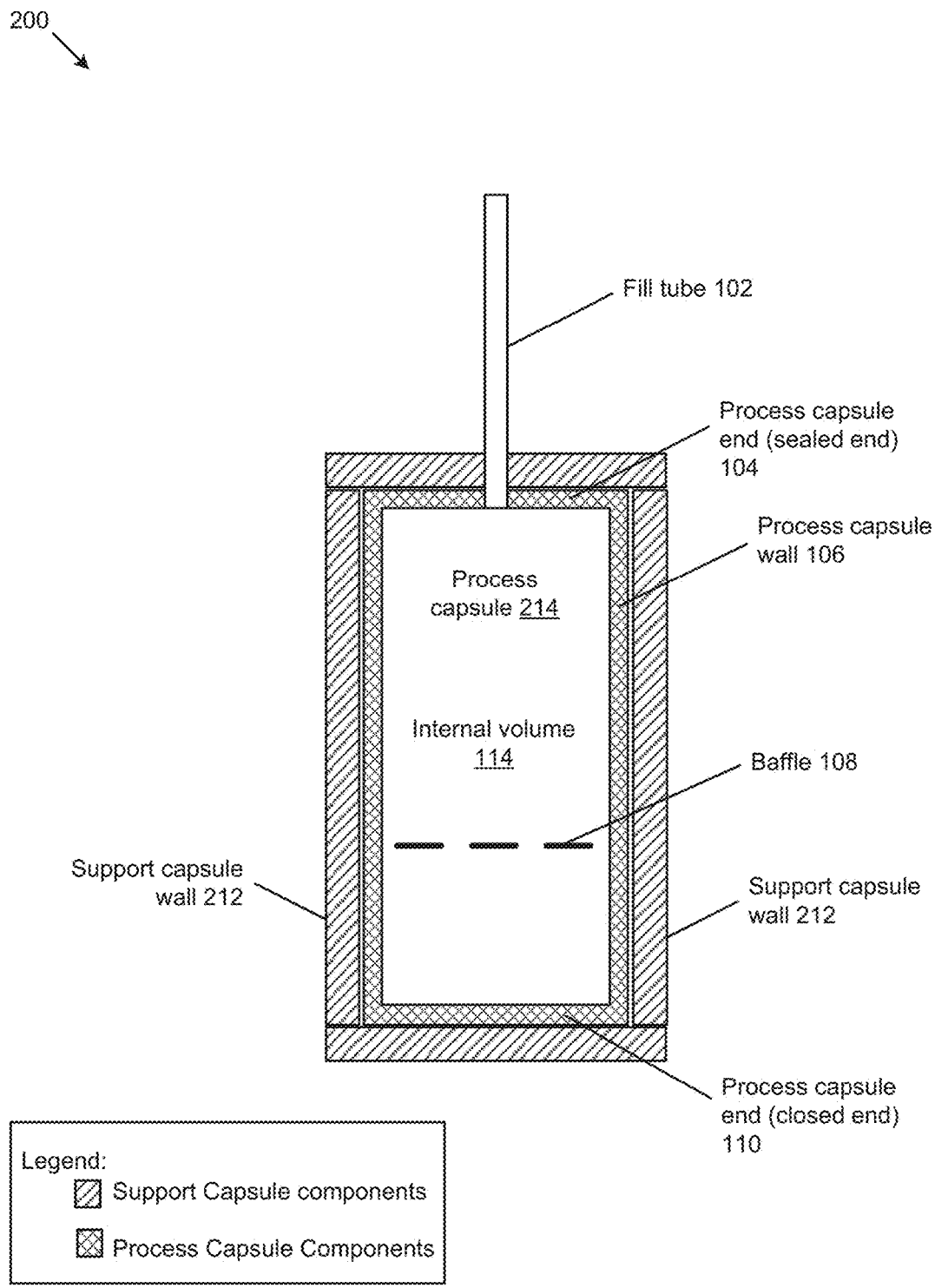
FIG. 2 is a diagram showing a dual capsule design wherein a process capsule is disposed within a support capsule, according to some embodiments.
Figure 3:
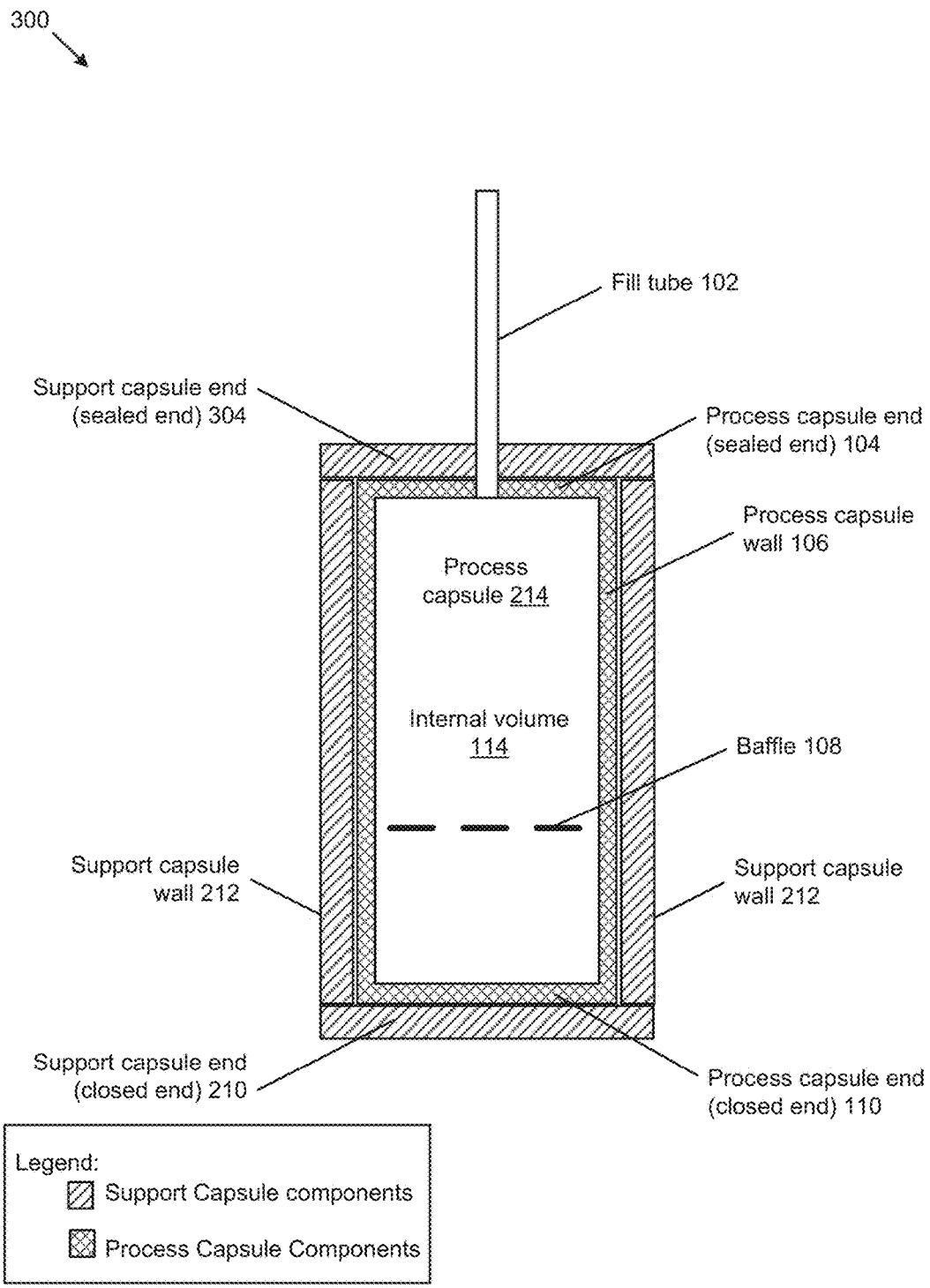
FIG. 3 is a diagram of a dual capsule where a process capsule is disposed within a support capsule, according to some embodiments.

FIG. 2 is a diagram 200 showing a dual capsule design (which may be referred to simply as a "capsule") wherein a process capsule 214 is disposed within a support capsule having a support capsule wall 212. The support capsule provides structural support for the process capsule. Furthermore, process capsule 214 may also be provided with at least one baffle 108 within internal volume 114, the one or more baffles 108 serving to create separate regions within the internal volume 114. In one embodiment, as shown in FIG. 3, the support capsule comprises a support capsule closed end 210, at least one support capsule wall 212 adjoining the support capsule closed end 210 and extending therefrom, and a support capsule sealed end 304 adjoining the at least one support capsule wall 212 and opposite of the support capsule closed end 110. "Support capsule closed end", "support capsule wall", and "support capsule sealed end" are terms of convenience and should not be considered limiting terms. The support capsule closed end 210, at least one support capsule wall 212, and the support capsule sealed end 304 define an internal volume capable of receiving and containing a process capsule. The process capsule possesses a process capsule closed end 110, at least one process capsule wall 106 adjoining the process capsule closed end 110 and extending therefrom, and a process capsule sealed end 104 adjoining the at least one process capsule wall and opposite of the process capsule closed end 110. The process capsule closed end 110, at least one process capsule wall 106, and the process capsule sealed end 104 define an internal volume 114 within the process capsule capable of containing at least one material and at least one solvent that becomes a supercritical fluid at a high temperature and high pressure condition (also referred to as "HPHT"). HPHT conditions encompass temperatures greater than about room temperature (about 20° C.) and pressures greater than about 1 atmosphere. In one embodiment, the capsule possesses a cylindrical member or shape. Process capsule 214 may also be provided with at least one baffle 108 within internal volume 114, the one or more baffles 108 serving to create separate regions within the internal volume 114. The separate regions are in fluid communication with each other since the one or more baffles will typically have a cross-sectional area smaller than the area defined by the inner diameter of the capsule, thereby producing a fractional open area of the baffle. In a specific embodiment, baffle 108 has a fractional open area of between about 0.5% and about 75%, but can also have other percentages. The baffle material may comprise copper, copper-based alloy, gold, silver, palladium, platinum, platinum-based alloy, iridium, ruthenium, rhodium, osmium, titanium, vanadium, chromium, chromium-based alloy, iron, iron-based alloy, nickel, nickel-based alloy, zirconium, niobium, molybdenum, tantalum, tungsten, rhenium, silica, alumina, combinations of any of the foregoing, and the like.

The structural support capsule may be required to prevent substantial deformation, strain, cracks, leaks, and failure of the process capsule due to the longitudinal and radial stresses that result from heating the process capsule after filling the process capsule with a solvent. The solvent (or fluid) within the process capsule will have a particular vapor pressure as dictated by the specific fluid type and its temperature, and this pressure can result in significant stresses on the process capsule, especially for capsules with one or more large dimensions. The present disclosure enables the inner process capsule to be pressurized without significant yielding or bowing of the capsule that potentially results in process capsule failure. Some bowing of the process capsule may occur, but not enough to result in process capsule failure. Instead, according to the disclosure, the process capsule is supported by the support capsule.

The support capsule prevents cracks, leaks, and catastrophic failure of the process capsule for the instances when the process capsule does experience some yielding or bowing. The outer support capsule may comprise steel, stainless steel, carbon steel, nickel, nickel-based alloy, Inconel® nickel-chromium and iron alloy, Hastelloy® nickel-molybdenum-chromium alloy, René® 41 nickel-based alloy, Waspalloy® nickel-based alloy, Mar-M 247® polycrystalline cast nickel-based alloy, Monel® nickel-copper alloy, Stellite® cobalt-chromium alloy, copper, copper-based alloy, zirconium, niobium, molybdenum, tantalum, tungsten, rhenium, platinum, platinum-based alloy, palladium, iridium, ruthenium, rhodium, osmium, titanium, vanadium, chromium, chromium-based alloy, iron, iron-based alloy, gold, silver, or aluminum, combinations of of any of the foregoing, and the like. The process capsule may comprise copper, copper-based alloy, gold, silver, palladium, platinum, platinum-based alloy, iridium, ruthenium, rhodium, osmium, titanium, vanadium, chromium, chromium-based alloy, iron, iron-based alloy, nickel, nickel-based alloy, zirconium, niobium, molybdenum, tantalum, tungsten, rhenium, combinations of any of the foregoing, and the like. In one embodiment of the present disclosure, the process capsule i may be constructed of a deformable material that enables the process capsule to expand when pressurized by the at least one solvent within the capsule. In one embodiment, the support capsule is constructed to have a yield strength which, when taken in combination with the process capsule, exceeds that of the stress exerted on the capsule by the vapor pressure and temperature of a fluid (or solvent) disposed within the process capsule. In one embodiment, the support capsule has a yield strength that exceeds that of the stress exerted on the capsule by the vapor pressure and temperature of a fluid (or solvent) disposed within the process capsule. In one embodiment, the support capsule is formed from one or more materials with a higher Young's modulus than the Young's modulus of a material of the process capsule. In one embodiment, the support capsule is formed from one or more materials with a higher yield strength than the yield strength of a material of the process capsule. In a specific embodiment, the support capsule has a higher yield strength than the yield strength of the process capsule. In a specific embodiment, the support capsule has a higher Young's modulus than the Young's modulus of the process capsule. In one embodiment, the support capsule is chosen to have a yield strength that exceeds that of the longitudinal stress exerted on the support capsule by the process capsule.

In a specific embodiment, as shown in the diagram 300 of FIG. 3, the process capsule has at least one fill tube 102 disposed on a portion of the process capsule sealed end. In a specific embodiment, the fill tube 102 has an opening operably coupled to the interior region (e.g., internal volume) of the process capsule. In a specific embodiment, and as shown in the diagram of FIG. 7, the process capsule has at least one fill tube 102 disposed on a portion of the process capsule closed end. In a specific embodiment, and as shown in the diagram of FIG. 7, the process capsule has at least one fill tube 102 disposed on a portion of the process capsule sealed end and the process capsule has at least one fill tube 102 disposed on a portion of the process capsule closed end. As also shown in one embodiment, the capsule has a first support capsule closed end 210 integrally coupled to the process capsule closed end, a second support capsule sealed end 304 integrally coupled to the process capsule sealed end, and a third support capsule wall 212 integrally coupled to the process capsule wall. In a specific embodiment, the first support capsule closed end, second support capsule sealed end, and third support capsule wall are configured to maintain a cylindrical shape of the process capsule free from any substantial deformation. In one embodiment, the support capsule ends (e.g., support capsule sealed end 304 and support capsule closed end 210) are chosen to integrally couple or mate with the process capsule.

The support capsule may be constructed and applied to support the process capsule 214 in multiple ways. The support capsule wall may be constructed from a single tube, rolled and welded from sheet material, or composed of multiple segments to form a support capsule wall that may provide radial support. The multiple segments may be stacked vertically and/or radially to provide structural support. Multiple wall components may be brazed, welded, glued, cemented, interference fit or otherwise bonded together to form the support capsule wall. The support capsule wall may have a thickness greater than 0.001 inch, greater than 0.01 inch, greater than 0.1 inch, greater than 0.250 inch, greater than 0.5 inch, greater than 1 inch, greater than 2 inch, or greater than 5 inch. The support capsule wall may cover any fraction of the process capsule wall, but may be over the entire wall of the process capsule, and may extend over the process capsule ends (sealed end and closed end). In one embodiment, the support capsule wall is configured to have an inner diameter slightly larger than the outer diameter of the process capsule. This enables the process capsule to be mechanically coupled to the wall of the support capsule, and furthermore, the process capsule may be slidably inserted into the support capsule. The inner diameter of the support capsule wall be larger than the outer diameter of the process capsule by greater than 0.0001 inch, greater than 0.001 inch, greater than 0.01 inch, greater than 0.1 inch, greater than 0.25 inch, greater than 0.5 inch, or greater than 1 inch.

Each support capsule ends, each of which may be referred to as a cap device, may be formed from one piece of material or from multiple pieces of material. If multiple pieces are used to construct one or more of the support capsule ends, the pieces may be brazed, welded, glued, cemented, interference fitted, bonded, or mechanically held together. The thickness of the support capsule ends may be between about 0.05 inches and 30 inches, although other thicknesses may also be used. The support capsule ends may be in any shape or form but are typically chosen to mate with the process capsule ends. In one embodiment, the diameter of one or more of the support capsule ends may be approximately equal to the diameter of the process capsule, particularly the process capsule ends. In another embodiment, one or more of the support capsule ends may be larger in diameter than the process capsule ends to accommodate attachment of the support capsule ends to the support capsule wall. In another embodiment, one or more of the support capsule ends may be smaller in diameter than the process capsule ends. In one embodiment, one or more of the support capsule ends may extend over the process capsule wall to provide structural support.

The support capsule ends may be attached to the support capsule wall by one or more of welding, tungsten inert gas (TIG) welding, orbital welding, arc welding, e-beam welding, ultrasonic welding, magnetic pulse welding, torch welding, vibratory welding, pinch sealing, brazing, cold welding, among other techniques. The braze alloy may comprise at least one of copper, silver, gold, nickel, or palladium. The braze may be applied as a foil with a thickness between 0.001 inch and 0.025 inch and the bond may be effected by heating the process capsule/braze/support capsule above the liquidus temperature of the braze alloy under a suitable atmosphere, such as argon, argon/hydrogen, or hydrogen. The support capsule ends may also be attached to the support capsule wall through the use of fasteners, bolts, threads, retaining rings, constant section rings, threaded screws, springs, wave springs, among other techniques.

In one embodiment, the support capsule wall and one or more of the support capsule ends may be formed from a single piece of material. In one embodiment, the support capsule closed end and support capsule wall are constructed from one piece of material and then the support capsule sealed end is attached to the support capsule wall, for example, after insertion of the process capsule. The support capsule closed end and wall assembly may be formed by a variety of processes including extruding, drawing, rolling, casting, machining, welding, among other fabrication techniques.

In one embodiment, the process capsule is disposed within the support capsule after attachment of the support capsule closed end to the support capsule wall and prior to attachment of the support capsule sealed end to the support capsule wall. After insertion of the process capsule, the support capsule sealed end is then attached to the support capsule. In an alternative embodiment, the process capsule (either fully or assembled or during the assembly process) is placed within the support capsule wall, and subsequently, the two support capsule ends are attached, either sequentially or simultaneously.

The support capsule may be brazed, welded, glued, cemented, interference fitted, or otherwise bonded to the process capsule. Any part of the support capsule (support capsule wall, support capsule closed end, support capsule sealed end) may be brazed, welded, glued, cemented, interference fit, or otherwise bonded to any part of the process capsule (process capsule wall, process capsule closed end, process capsule sealed end). For example, the support capsule sealed end may be attached or bonded to process capsule sealed end. Or, in another example, the process capsule wall may be attached or bonded to the support capsule closed end. The bonding or attachment may be over a small fraction of the component or the entire component for each of the support capsule and process capsule components. The braze alloy may comprise at least one of copper, silver, gold, nickel, or palladium. The braze may be applied as a foil with a thickness between 0.001 inch and 0.025 inch and the bond may be effected by heating the process capsule/braze/support capsule above the liquidus temperature of the braze alloy under a suitable atmosphere, such as argon, argon/hydrogen, or hydrogen.

In one embodiment, a material may be placed between the process capsule and the support capsule. One or more materials may be placed between the support capsule ends and the process capsule ends. One or more materials may be placed between the support capsule wall and the process capsule wall. One or more materials may be placed between the process capsule wall and the support capsule ends. One or more materials may be placed between the process capsule ends and the support capsule wall. Materials placed between the process capsule and the support capsule may comprise steel, stainless steel, carbon steel, nickel, nickel-based alloy, Inconel® nickel-chromium and iron alloy, Hastelloy® nickel-molybdenum-chromium alloy, René® 41 nickel-based alloy. Waspalloy® nickel-based alloy. Mar-M 247® polycrystalline cast nickel-based alloy, Monel® nickel-copper alloy, Stellite® cobalt-chromium alloy, copper, copper-based alloy, zirconium, niobium, molybdenum, molybdenum disulfide, tantalum, tungsten, rhenium, platinum, platinum-based alloy, palladium, iridium, ruthenium, rhodium, rhenium, osmium, sulfur, tantalum, titanium, vanadium, chromium, iron, iron-based alloy, gold, silver, $MC_x$-$N_yO_z$, wherein M is at least one of aluminum, boron silicon, titanium, vanadium, chromium, yttrium, zirconium, lanthanum, a rare earth metal, hafnium, tantalum, tungsten, and wherein each of x, y, and z is between 0 and 3 (i.e., 0<x, y, z<3), aluminum, graphite, graphite foil, salt, boron nitride, anti-seize lubricant, beryllium, magnesium, calcium, strontium, barium, lithium, sodium, potassium, rubidium, cesium, combinations of any of the foregoing, among other materials. One or more other elements, compounds, materials, or chemical additives may be disposed between the process capsule and the support capsule. The space between the process capsule and the support capsule also may be filled with a solvent or fluid such as air, oxygen, hydrogen, ammonia, argon, water, nitrogen, helium, nitrous oxide, carbon dioxide, methane, ethane, propane, ethylene, propylene, methanol, isopropanol, acetic acid, benzene, toluene, ethanol, acetone, a combination of any of the foregoing, and the like. In one embodiment of the disclosure, the one or more types of solvent and their associated volumetric fills are chosen so that before and during the high pressure and high temperature process the fluid between the process capsule and the support capsule produces a pressure to either counterbalance the pressure from within the process capsule or to provide an overpressure so that the process capsule is under a compressive or neutral stress, rather than under tensile stress. In an alternative embodiment, the space between the support capsule and the process capsule is evacuated and at a pressure below atmospheric pressure.

In one embodiment of the present disclosure, the capsule which is a process capsule disposed within a support capsule may be heated and used to process a material in a supercritical fluid. The capsule may be used to process a variety of materials, including, but not limited to, gallium nitride single crystals.

According to the present disclosure, the capsule which is a process capsule disposed within a support capsule may be placed in a pressure apparatus, such as an autoclave, "zero-stroke" pressure apparatus, or a pressure apparatus with a stroke. In one embodiment of the disclosure, the volume between the capsule and the pressure apparatus contains a solvent or fluid. The solvent or fluid may comprise air, oxygen, hydrogen, ammonia, argon, water, nitrogen, helium, nitrous oxide, carbon dioxide, methane, ethane, propane, ethylene, propylene, methanol, isopropanol, acetic acid, benzene, toluene, ethanol, acetone, a combination thereof, and the like. In one embodiment of the disclosure, the one or more types of solvent and their associated volumetric fills are chosen so that during the high pressure and high temperature process the fluid between the capsule and the pressure vessel produces a pressure to either counterbalance the pressure from within the capsule or to provide an overpressure so that the capsule is under a compressive or neutral stress, rather than under tensile stress. Furthermore, the volume (or space) between the capsule and the pressure device may contain another material. The material may comprise steel, stainless steel, carbon steel, nickel, nickel-based alloy, Inconel® nickel-chromium and iron alloy, Hastelloy® nickel-molybdenum-chromium alloy, René® 41 nickel-based alloy, Waspalloy® nickel-based alloy, Mar-M 247® polycrystalline cast nickel-based alloy, Monel® nickel-copper alloy, Stellite® cobalt-chromium alloy, copper, copper-based alloy, zirconium, niobium, molybdenum, molybdenum disulfide, tantalum, tungsten, rhenium, platinum, platinum-based alloy, palladium, iridium, ruthenium, rhodium, rhenium, osmium, sulfur, tantalum, titanium, vanadium, chromium, iron, iron-based alloy, gold, silver, aluminum, graphite, graphite foil, salt, boron nitride, anti-seize lubricant, beryllium, magnesium, calcium, strontium, barium, lithium, sodium, potassium, rubidium, cesium, combinations thereof, among other materials.

The present disclosure further discloses methods for processing materials in a supercritical fluid with a process capsule disposed within a support capsule. One such embodiment is: Load at least one material into the interior volume of a process capsule; Load the process capsule into a support capsule; Fill the interior volume of the process capsule with solvent; Seal the process capsule; Heat the process capsule to generate a supercritical fluid; Cool the process capsule; Remove material from the process capsule; and Perform other steps as desired. This sequence of steps provides a method according to an embodiment of the disclosure. Other alternatives can also be provided where steps are added, one or more steps are removed, or one or more steps are provided in a different sequence.

Another method for processing materials in a supercritical fluid with a process capsule disposed within a support capsule is as follows: Load at least one material into the interior volume of a process capsule; Fill the interior volume of the process capsule with solvent; Seal the process capsule; Load the process capsule into a support capsule; Heat the process capsule to generate a supercritical fluid; Cool the process capsule; Remove material from the process capsule; and Perform other steps as desired. This sequence of steps provides a method according to an embodiment of the disclosure. In this embodiment, it is preferable to maintain the process capsule at a low temperature until it is disposed within the support capsule to create a low pressure within the process capsule and prevent substantial process capsule deformation and possible failure. Other alternatives can also be provided where steps are added, one or more steps are removed, or one or more steps are provided in a different sequence.

Another method for processing materials in a supercritical fluid with a process capsule disposed within a support capsule is as follows: Load the process capsule into a support capsule; Load at least one material into the interior volume of a process capsule; Fill the interior volume of the process capsule with solvent; Seal the process capsule; Heat the process capsule to generate a supercritical fluid; Cool the process capsule; Remove material from the process capsule; and Perform other steps as desired. This sequence of steps provides a method according to an embodiment of the disclosure. Other alternatives can also be provided where steps are added, one or more steps are removed, or one or more steps are provided in a different sequence.

Another method for processing materials in a supercritical fluid with a process capsule disposed within a support capsule is as follows: Load at least one material into the interior volume of a process capsule, the process capsule has a closed end and an open end; Attach a process capsule sealed end to the open end of the process capsule; Load the process capsule into a support capsule, the support capsule has a closed end and an open end; Attach a support capsule sealed end to the open end of the support capsule; Fill the interior volume of the process capsule with solvent; Seal the process capsule; Heat the process capsule to generate a supercritical fluid; Cool the process capsule; Remove material from the process capsule; and Perform other steps as desired. This sequence of steps provides a method according to an embodiment of the disclosure. Other alternatives can also be provided where steps are added, one or more steps are removed, or one or more steps are provided in a different sequence.

Another method for processing materials in a supercritical fluid with a process capsule disposed within a support capsule is as follows: Load at least one material into the interior volume of a process capsule, the process capsule has a closed end and an open end; Attach a process capsule sealed end to the open end of the process capsule; Load the process capsule into a support capsule, the support capsule has two open ends; Attach a support capsule closed end to one open end of the support capsule; Attach a support capsule sealed end to the open end of the support capsule; Fill the interior volume of the process capsule with solvent; Seal the process capsule; Heat the process capsule to generate a supercritical fluid; Cool the process capsule; Remove material from the process capsule; and Perform other steps as desired. This sequence of steps provides a method according to an embodiment of the disclosure. Other alternatives can also be provided where steps are added, one or more steps are removed, or one or more steps are provided in a different sequence.

In another aspect of the present disclosure, additional methods for forming the support capsule or the process capsule are disclosed. Specifically, methods for attaching the process capsule ends to the process capsule wall and for attaching the support capsule ends to the support capsule wall are disclosed. One technique for attaching the ends to the walls of the capsules is to form a butt joint by orbital welding. Orbital welding is a welding process by which the arc is mechanically rotated by 360 degrees around a static work piece. The butt joint may be a square butt joint or a non-square butt-joint, where the joining surfaces may have any shape, geometry or configuration. In one embodiment, the joining surfaces are rounded. The orbital welding of the butt joint may be used to join components of the process capsule or the support capsule. Specifically, orbital welding may be used for attaching the process capsule ends to the process capsule wall and/or for attaching the support capsule ends to the support capsule wall.

Figure 4:
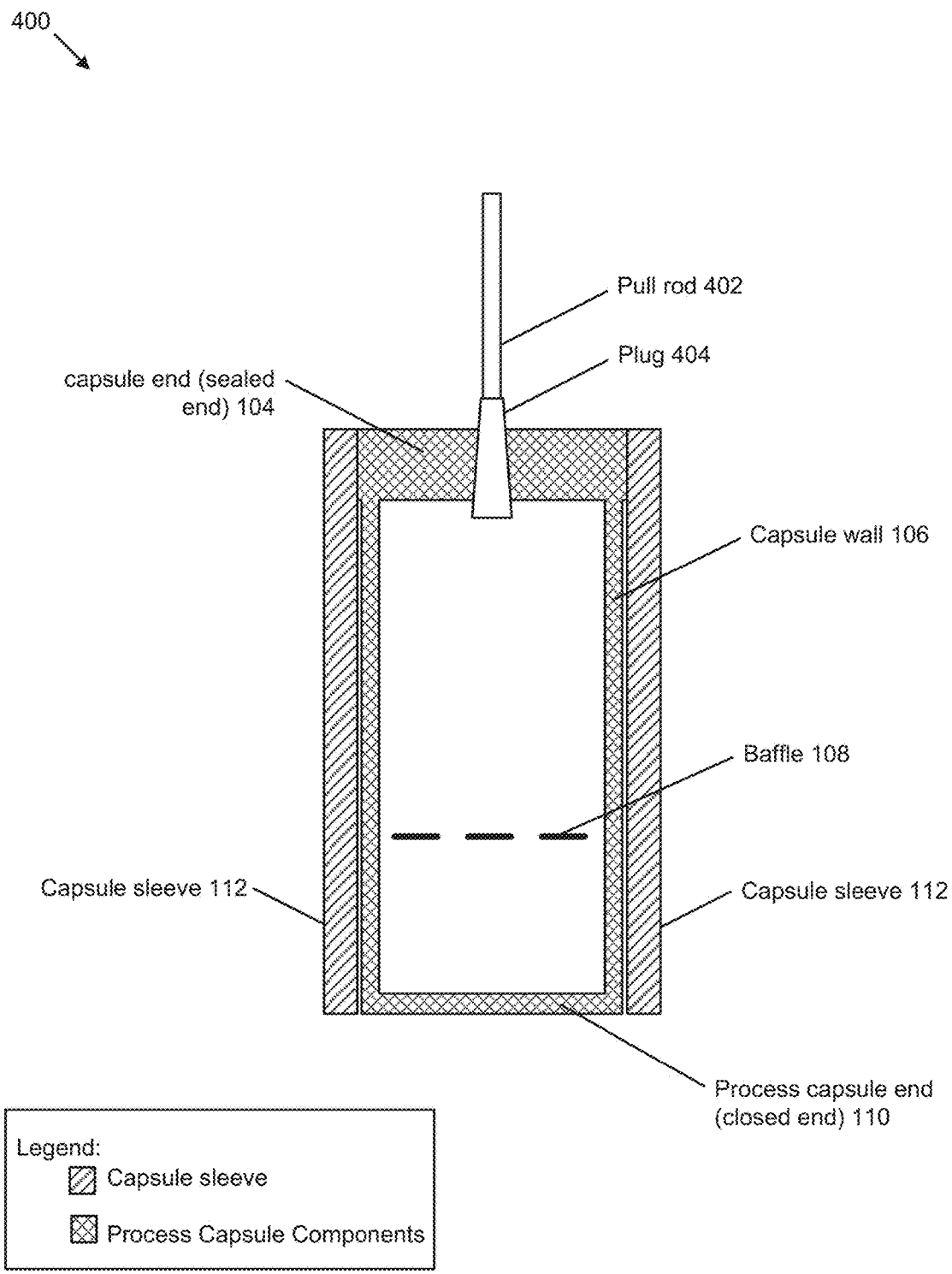
FIG. 4 is a diagram of a capsule with a tapered pressure seal, according to some embodiments.

The diagram 400 of FIG. 4 further provides a capsule that does not require a fill tube. In the embodiment shown, a capsule uses a tapered pressure seal where a tapered plug is positioned in a tapered hole (seat) with the narrow end toward the outside of the capsule. A pull rod 402, integral to the plug 404, extends beyond the filling attachment through a sliding seal (or bellows or other seal) that prevents vapor from the solvent within the capsule from escaping or air (or other gas) or other material from outside the capsule from entering the capsule. By pulling up on the pull rod 402 the capsule may be sealed. The plug is pulled up against the seat with sufficient force as to deform the softer of the two materials, thereby producing a hermetic seal. This seal prevents vapor from the solvent within the capsule from escaping or air (or other gas) or material from entering the capsule. Pressure buildup inside the capsule serves to increase the sealing force, thereby improving the seal. Taper angles may be chosen to facilitate deformation of the softer material, and may be in a range of near-normal to near-parallel to the direction of motion of the plug.

Figure 5:
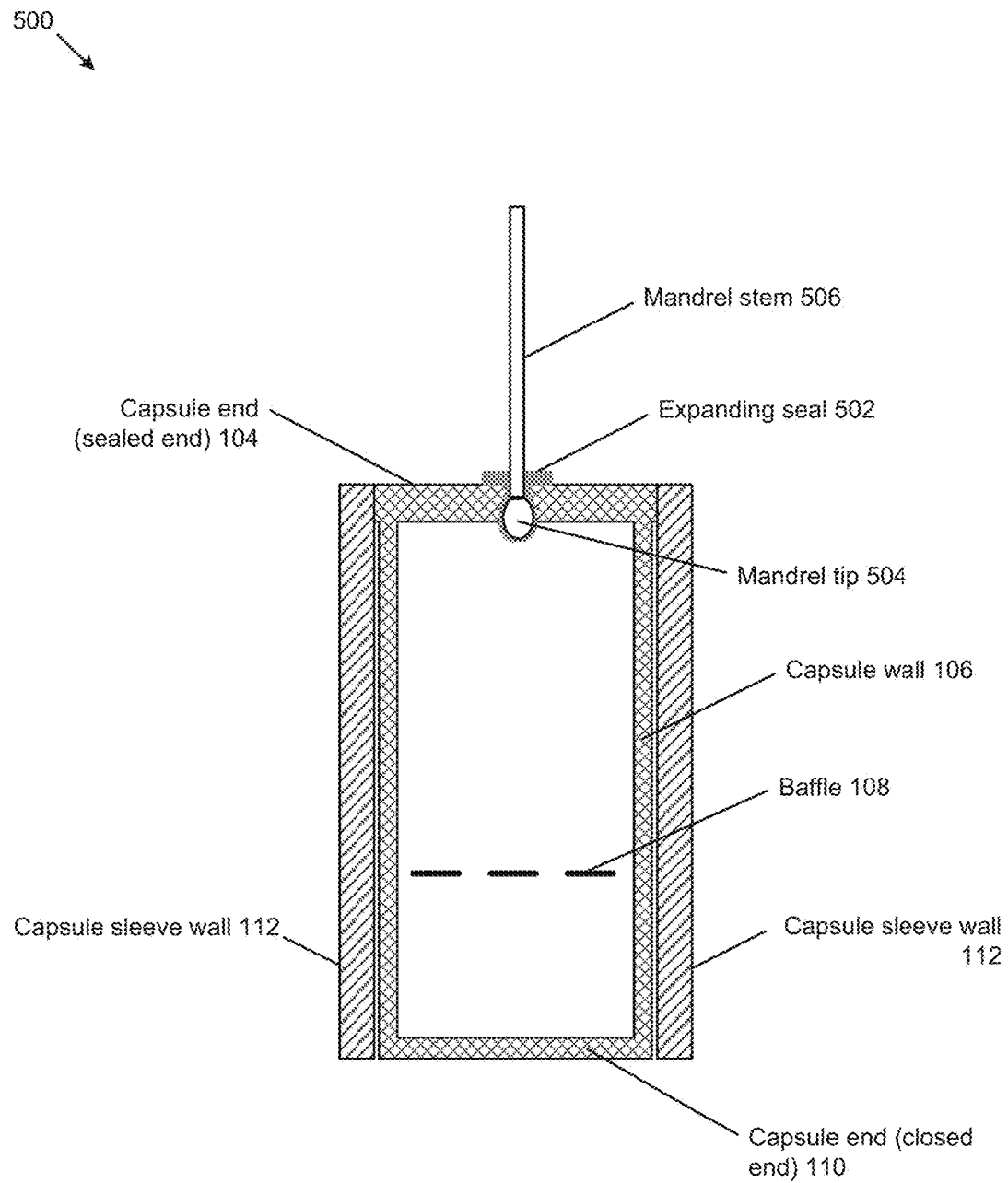
FIG. 5 is a diagram of a capsule with a plug seal, according to some embodiments.

In another embodiment, a capsule, as shown in the diagram 500 of FIG. 5, includes an internally-expanding seal 502 to serve as a closed-end plug in order to seal the capsule after solvent filling, whereby a mandrel consisting of a mandrel tip 504 and a mandrel stem 506 contained inside the expanding seal 502 is pulled upwards against the expanding seal 502 and capsule body (or capsule end), causing the material of the expanding seal 502 to expand and fill the hole in the top of the capsule in which it is inserted. The mandrel tip 504 is made of a material harder than the body of the expanding seal 502 so that the expanding seal 502 expands sufficiently to produce the hermetic seal when pulled with sufficient force. The mandrel stem 506 is made of a material with sufficient tensile strength to provide the necessary force on the mandrel tip to expand the expanding seal 502.

Figure 6:
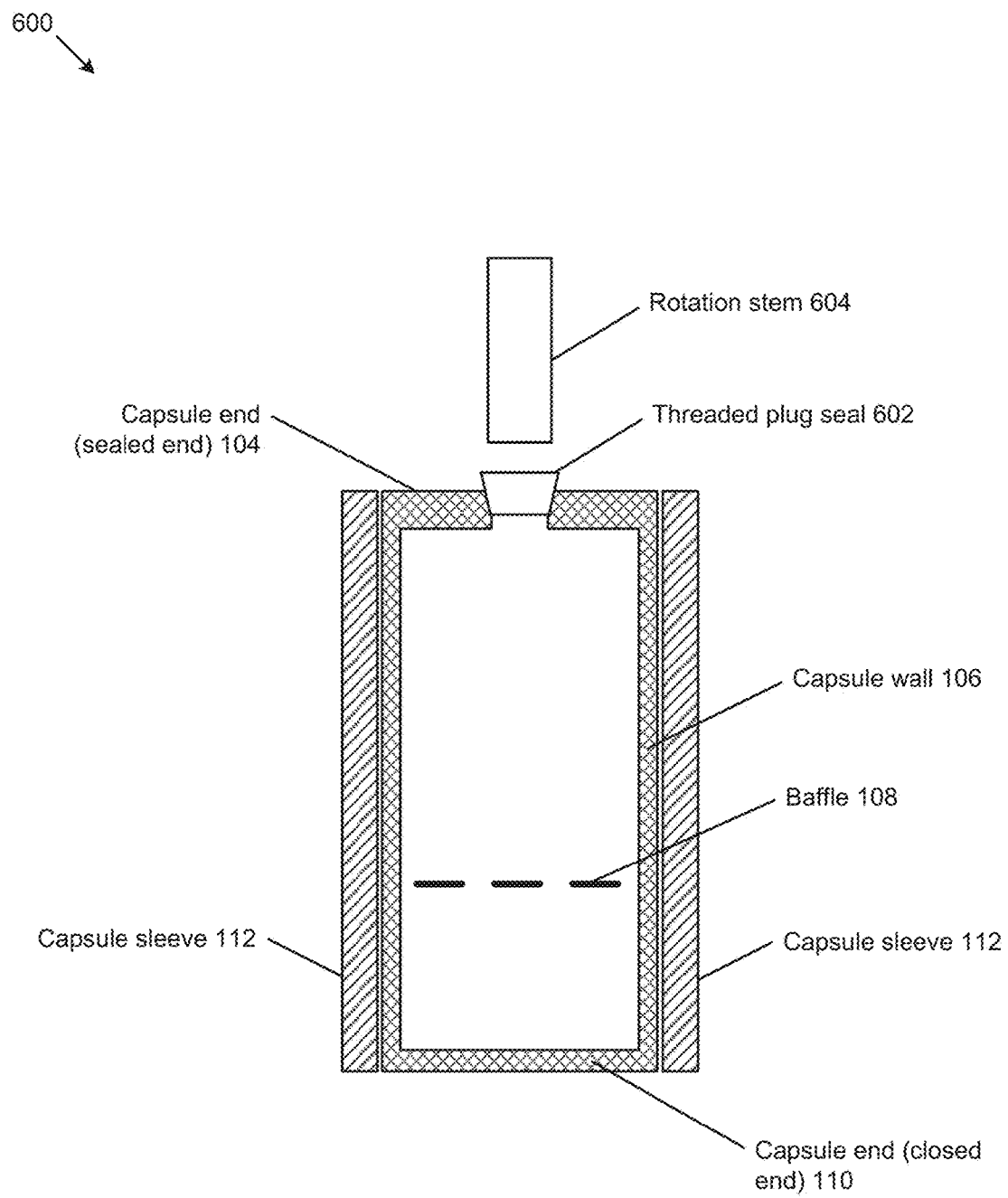
FIG. 6 is a diagram of a capsule with a tapered threaded plug, according to some embodiments.

In another embodiment, a capsule, as shown in the diagram 600 of FIG. 6, includes a tapered threaded plug seal 602 to produce a capsule seal after solvent filling. By rotating the threaded plug through a rotating seal, or bellows seal, the capsule may be hermetically sealed. The plug is made of a harder or softer material than the tapered threaded seat, which is made of a softer or harder material than the plug, respectively. The seal can be rotated using a rotation stem 604, as shown.

In the present disclosure, sealing of the capsule (e.g., the process capsule) may be performed by one or more of welding, tungsten inert gas (TIG) welding, orbital welding, arc welding, e-beam welding, ultrasonic welding, magnetic pulse welding, torch welding, vibratory welding, pinch sealing, brazing, cold welding, among other techniques.

The methods and apparatuses disclosed in the present disclosure may be utilized to produce material within a supercritical fluid. This material may be subsequently used to produce wafers, such as crystalline wafers, and in particular, gallium nitride wafers. In one or more embodiments, the present wafer may be utilized to fabricate devices such as optoelectronic devices, lasers, light emitting diodes, solar cells, photodetectors, and integrated circuits, transistor devices, other device structures, photoelectrochemical water splitting and hydrogen generation, and others. In one embodiment the present wafer could be used to deposit an n-type gallium nitride layer, a quantum well active region layer or layers, and a p-type gallium nitride layer which comprise an LED device. It can be known from the literature that such a device or devices fabricated on the high-quality, low-dislocation-density, gallium nitride substrate (or wafer) will offer superior device performance. These devices can additionally be made in a cost-effective manner on the wafer provided herein.

FIG. 7 is a diagram 700 of a capsule with configurations of fill tubes. Multiple fill tubes may be disposed normal to any surface (as shown normal to the process capsule end), or fill tubes can be disposed at an offset angle relative to any surface, including the process capsule end surfaces and the process capsule wall surface.

Figure 8:
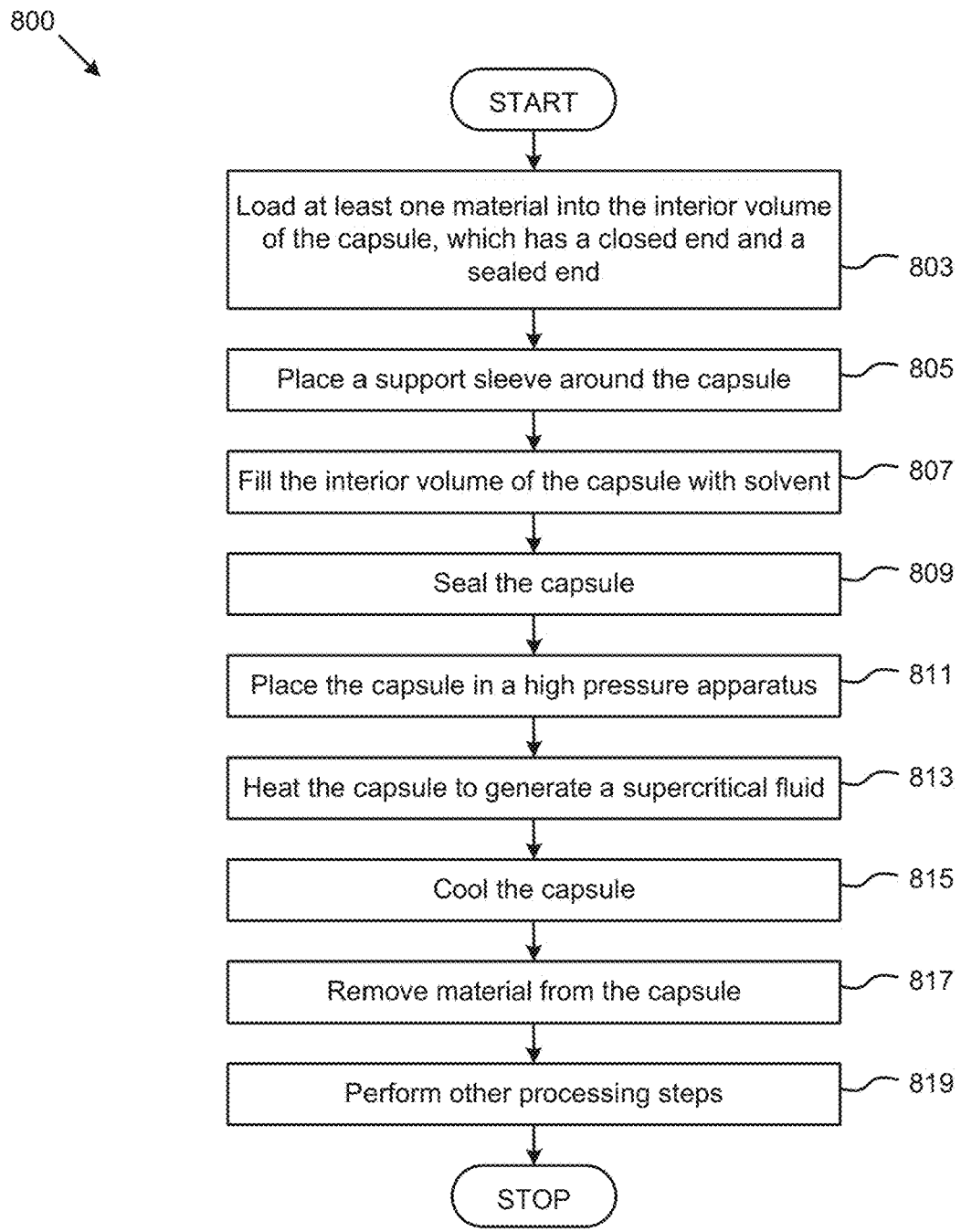
FIG. 8 shows method steps that can be practiced while using a capsule for high pressure, high temperature processing according to various embodiments.

FIG. 8 shows method steps 800 that may be practiced while using a capsule for high pressure, high temperature processing. Techniques for processing materials in supercritical fluids within a capsule with a support capsule sleeve may be described in terms of method steps as shown in FIG. 8: Load at least one material into the interior volume of the capsule, which has a closed end and a sealed end (see step 803); Place a support sleeve around the capsule (see step 805); Fill the interior volume of the capsule with solvent (see step 807); Seal the capsule (see step 809); Place the capsule in a high pressure apparatus (see step 811); Heat the capsule to generate a supercritical fluid (see step 813); Cool the capsule (see step 815); Remove material from the capsule (see step 817); and Perform other steps as desired (see step 819). This sequence of steps provides a method according to an embodiment of the disclosure. Other alternatives can also be provided where steps are added, one or more steps are removed, or one or more steps are provided in a different sequence.

Figure 9:
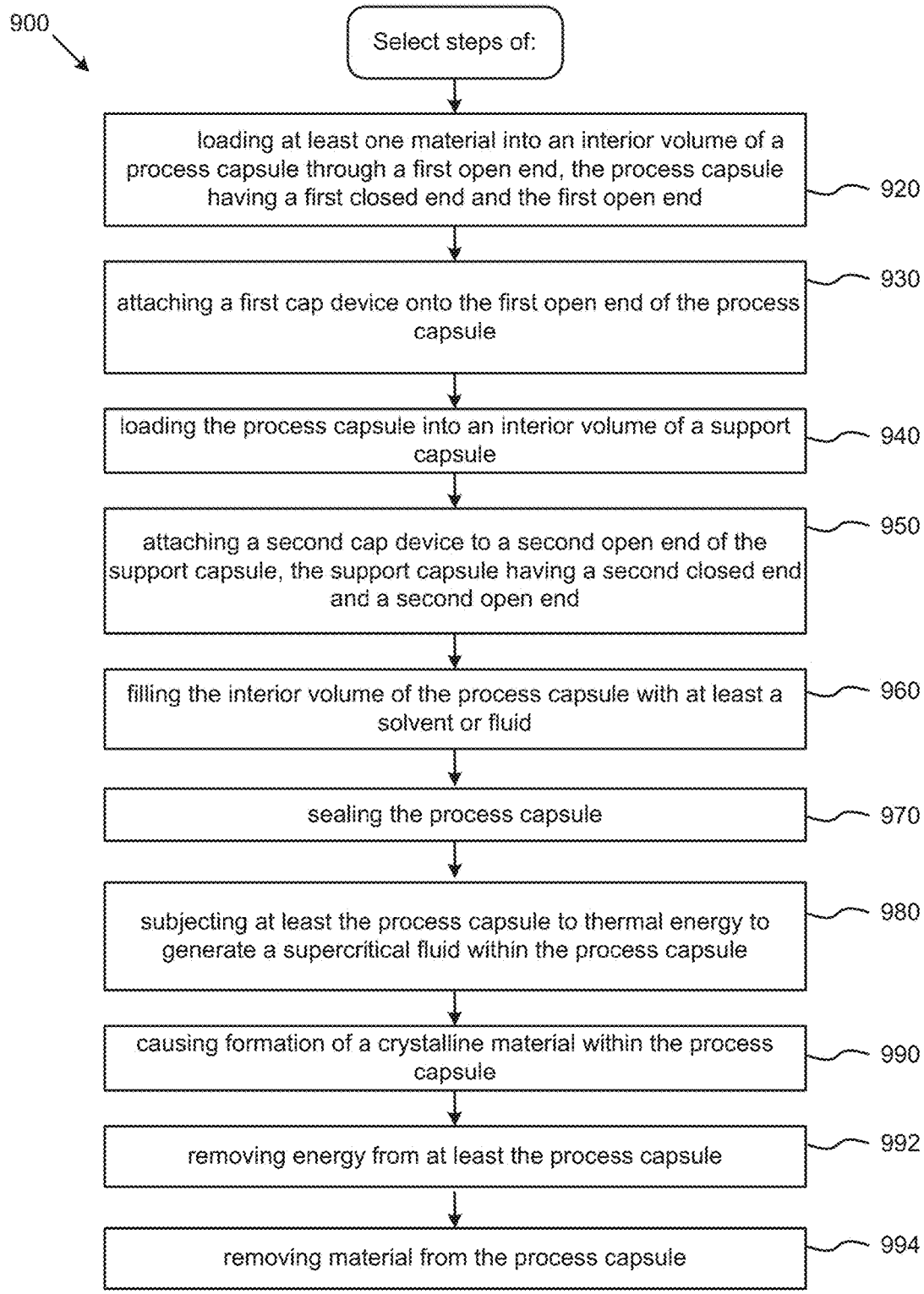
FIG. 9 shows method steps that can be practiced while using a capsule for high pressure, high temperature processing according to various embodiments.

FIG. 9 shows method steps that may be practiced while using a capsule for high pressure, high temperature processing. As an option, the present system 900 may be implemented in the context of the architecture and functionality of the embodiments described herein. Of course, however, the system 900 or any operation therein may be carried out in any desired environment. As shown, an operation may be implemented in whole or in part using program instructions accessible by a module. The modules can be connected to a communication path, and any operation can communicate with other operations over said communication path. The modules of the system can, individually or in combination, perform method operations within system 900. Any operations performed within system 900 may be performed in any order unless as may be specified in the claims. The embodiment of FIG. 9 implements modules to perform: loading at least one material into an interior volume of a process capsule through a first open end, the process capsule having a first closed end and the first open end (see module 920); attaching a first cap device onto the first open end of the process capsule (see module 930); loading the process capsule into an interior volume of a support capsule (see module 940); attaching a second cap device to a second open end of the support capsule, the support capsule having a second closed end and a second open end (see module 950); filling the interior volume of the process capsule with at least a solvent or fluid (see module 960); sealing the process capsule (see module 970); subjecting at least the process capsule to thermal energy to generate a supercritical fluid within the process capsule (see module 980); causing formation of a crystalline material within the process capsule (see module 990); removing energy from at least the process capsule (see module 992); and removing material from the process capsule (see module 994).

Certain embodiments provided by the present disclosure comprise a capsule apparatus for processing a material in a supercritical fluid comprising: a process capsule comprised of a closed end, the closed end being characterized by a first Young's modulus and a first yield strength, a wall, the wall being characterized by a second Young's modulus and a second yield strength, and a sealed end, the sealed end being characterized by a third Young's modulus and a third yield strength, wherein the closed end, the wall, and the sealed end are configured to define an internal volume capable of receiving a material and a solvent; a support capsule comprised of a closed support end, the closed support end being characterized by a fourth Young's modulus and a fourth yield strength, a support capsule wall, the support capsule wall being characterized by a fifth Young's modulus and a fifth yield strength, and a sealed support end, the sealed support end being characterized by a sixth Young's modulus and a sixth yield strength, wherein the closed support end, support capsule wall, and sealed support end are configured to receive a process capsule; and the process capsule being disposed within the support capsule.

Certain embodiments provided by the present disclosure comprise a capsule for processing a material in a supercritical fluid comprising: a closed end; a sealable end; a wall that adjoins the closed end and extends therefrom, wherein the sealable end adjoins the wall, and wherein the closed end, sealable end, and wall produces an internal volume that is configured to receive a material and a fluid; and a support sleeve disposed on at least the wall, closed end, or sealable end, which is configured to provide mechanical support for the capsule.

Certain embodiments provided by the present disclosure comprise a capsule for processing a material in a supercritical fluid comprising: a cylindrical member, the cylindrical member comprising a first end and a second end and a length; a closed end provided at the first end; a sealed end provided at the second end; a support sleeve disposed on at least the cylindrical member, the closed end, or the sealed end, the support sleeve being characterized by a material thickness and a first Young's modulus and a first yield strength; and a fluid disposed within the capsule having a first temperature and a first vapor pressure.

Certain embodiments provided by the present disclosure comprise a capsule for processing a material in a supercritical fluid comprising: a cylindrical member, the cylindrical member comprising a first end and a second end and a length, the cylindrical member being characterized by a first Young's modulus and a first yield strength; a closed end provided at the first end, the closed end being characterized by a second Young's modulus and a second yield strength; a sealed end provided at the second end, the sealed end being characterized by a third Young's modulus and a third yield strength; a support sleeve disposed on at least the cylindrical member, the closed end, or the sealed end, the support sleeve being characterized by a fourth Young's modulus and a fourth yield strength.

Certain embodiments provided by the present disclosure comprise a capsule for processing a material in a supercritical fluid comprising: a wall having a first end and a second end and a length; a closed end disposed at the first end; a sealed end disposed at the second end; and a support sleeve disposed on the wall, closed end, or sealed end, wherein the support sleeve is configured to provide mechanical support for the capsule.

In certain embodiments of a capsule, the fluid may be added or removed from at least the process capsule closed end or the process capsule sealed end.

In certain embodiments of a capsule, the wall is characterized by a first yield strength, the support sleeve is characterized by a second yield strength, the second yield strength being greater than the first yield strength.

The capsule of embodiment 5, wherein the wall is characterized by a first Young's modulus, the support sleeve is characterized by a second Young's modulus, the second Young's modulus being greater than the first Young's modulus.

In certain embodiments of a capsule, the support sleeve comprises a material selected from steel, stainless steel, carbon steel, nickel, nickel-based alloy, Inconel® nickel-chromium and iron alloy, Hastelloy® nickel-molybdenum-chromium alloy, René® 41 nickel-based alloy, Waspalloy® nickel-based alloy, Mar-M 247® polycrystalline cast nickel-based alloy, Monel® nickel-copper alloy, Stellite® cobalt-chromium alloy, copper, copper-based alloy, zirconium, niobium, molybdenum, tantalum, tungsten, rhenium, platinum, platinum-based alloy, palladium, iridium, ruthenium, rhodium, osmium, titanium, vanadium, chromium, chromium-based alloy, iron, iron-based alloy, gold, silver, aluminum, and a combination of any of the foregoing.

In certain embodiments of a capsule, the wall, closed end, or sealed end comprises a material selected from copper, copper-based alloy, gold, silver, palladium, platinum, platinum-based alloy, iridium, ruthenium, rhodium, osmium, titanium, vanadium, chromium, chromium-based alloy, iron, iron-based alloy, nickel, nickel-based alloy, zirconium, niobium, molybdenum, tantalum, tungsten, rhenium, and a combination of any of the foregoing.

In certain embodiments of a capsule, the capsule further comprises providing a material disposed between the wall, closed end, or the sealed end and the support sleeve, the material being selected from at least one of nickel, rhodium, platinum, palladium, iridium, ruthenium, rhenium, tungsten, molybdenum, molybdenum disulfide, niobium, silver, sulfur, iridium, tantalum, $MC_xN_yO_z$, wherein M is at least one of aluminum, boron silicon, titanium, vanadium, chromium, yttrium, zirconium, lanthanum, a rare earth metal, hafnium, tantalum, tungsten, and wherein each of x, y, and z is between 0 and 3 (i.e., $0<x, y, z<3$), graphite, graphite foil, titanium, salt, boron nitride, or anti-seize lubricant, and combinations of any of the foregoing.

In certain embodiments of a capsule, the support sleeve is at least partially mechanically coupled to the closed end, wall, or sealed end.

In certain embodiments of a capsule, the coupling is caused by welding, brazing, gluing, cementing, or interference fitting.

In certain embodiments of a capsule, the capsule further comprises the closed end, wall, or sealed end being attached by welding, tungsten inert gas (TIG) welding, orbital welding, arc welding, e-beam welding, ultrasonic welding, magnetic pulse welding, torch welding, vibratory welding, pinch sealing, brazing, or cold welding.

In certain embodiments of a capsule, the attaching comprises orbital welding of a butt joint.

In certain embodiments of a capsule, the capsule further comprising a fluid within the capsule, wherein the support sleeve comprises a first yield strength, the first yield strength of the support sleeve configured to exceed the hoop stress exerted by the fluid at a temperature and pressure.

In certain embodiments of a capsule, the temperature is room temperature and the pressure is approximately 150 psi.

In certain embodiments of a capsule, the capsule further comprises a fluid within the capsule, wherein the support sleeve comprises a first yield strength, the first yield strength of the support sleeve configured to exceed the hoop stress exerted on the support sleeve by the wall of the capsule due to the fluid within the capsule at a temperature and pressure.

In certain embodiments of a capsule, the temperature is room temperature and the pressure is approximately 150 psi.

In certain embodiments of a capsule, the capsule further comprises providing a material disposed on the support sleeve, the material being selected from nickel, rhodium, platinum, palladium, iridium, ruthenium, rhenium, tungsten, molybdenum, molybdenum disulfide, niobium, silver, sulfur, iridium, tantalum, $MC_xN_yO_z$, wherein M is at least one of aluminum, boron silicon, titanium, vanadium, chromium, yttrium, zirconium, lanthanum, a rare earth metal, hafnium, tantalum, tungsten, and wherein each of x, y, and z is between 0 and 3 (i.e., $0<x, y, z<3$), graphite, graphite foil, titanium, salt, boron nitride, an anti-seize lubricant, and a combination of any of the foregoing.

While the above is a full description of the specific embodiments, various modifications, alternative constructions and equivalents may be used. Although the above has been described in terms of a specific embodiment, other techniques would be recognized by one of ordinary skill in the art. Therefore, the above description and illustrations should not be taken as limiting the scope of the disclosure which is defined by the appended claims.

What is claimed is:

1. A method for preparing a crystalline material in a supercritical fluid, the method comprising:
   disposing a process capsule into an interior volume of a support capsule, the process capsule comprising a first material and the support capsule comprising a second material;
   loading at least one fluid into said process capsule;
   sealing the process capsule, wherein the process capsule is sealed and the support capsule is left unsealed, said at least one fluid generating internal pressure in said sealed process capsule, said support capsule providing structural support for said sealed process capsule, enabling said sealed process capsule to be pressurized to 150 psi;
   disposing said support capsule containing said sealed process capsule in a high pressure apparatus; and
   heating the process capsule to a temperature between room temperature and 1500° C. to generate the supercritical fluid within the process capsule to form a crystalline material within the process capsule.

2. The method of claim 1, wherein the crystalline material comprises a [III-]nitride of a croup III element of the periodic table selected from GaN, AlN, InN, an alloy of any of the foregoing, and a combination of any of the foregoing.

3. The method of claim 1, further comprising removing thermal energy from the process capsule, wherein removing energy from the process capsule comprises reducing the temperature of the process capsule.

4. The method of claim 1, wherein sealing the process capsule is selected from welding, tungsten inert gas (TIG) welding, orbital welding, arc welding, e-beam welding, ultrasonic welding, magnetic pulse welding, torch welding, vibratory welding, pinch sealing, brazing, and cold welding.

5. The method of claim 1, wherein disposing said process capsule in said support capsule comprises attaching a cap device by at least one of welding, tungsten inert gas (TIG) welding, orbital welding, arc welding, e-beam welding, ultrasonic welding, magnetic pulse welding, torch welding, vibratory welding, pinch sealing, brazing, cold welding and the use of fasteners, bolts, threads, retaining rings, constant section rings, threaded screws, springs, or wave springs.

6. The method of claim 5, wherein the attaching comprises orbital welding of a butt joint.

7. The method of claim 1, further comprising providing a material disposed between the process capsule and the support capsule, the material selected from steel, stainless steel, carbon steel, nickel, nickel alloy, nickel-chromium and iron alloy, nickel-molybdenum-chromium alloy, polycrystalline nickel alloy, nickel-copper alloy, cobalt-chromium alloy, copper, copper alloy, zirconium, niobium, molybdenum, molybdenum disulfide, tantalum, tungsten, rhenium, platinum, platinum alloy, palladium, iridium, ruthenium, rhodium, rhenium, osmium, tantalum, titanium, vanadium, chromium, iron, iron alloy, gold, silver, aluminum, graphite, boron nitride, beryllium, magnesium, calcium, strontium, barium, lithium, rubidium, cesium, $MC_xN_yO_z$, wherein M is at least one of aluminum, boron silicon, titanium, vanadium, chromium, yttrium, zirconium, lanthanum, a rare earth metal, hafnium, tantalum, tungsten, and wherein each of x, y, and z is between 0 and 3 (i.e., $0<x, y, z<3$), and a combination of any of the foregoing.

8. The method of claim 1, further comprising providing a material disposed between the support capsule and a pressure apparatus, the material selected from steel, stainless steel, carbon steel, nickel, nickel alloy, nickel-chromium and iron alloy, nickel-molybdenum-chromium alloy, polycrystalline nickel alloy, nickel-copper alloy, cobalt-chromium alloy, copper alloy, zirconium, niobium, molybdenum, molybdenum disulfide, tantalum, tungsten, rhenium, platinum, platinum alloy, palladium, iridium, ruthenium, rhodium, rhenium, osmium, tantalum, titanium, vanadium, chromium, iron, ion alloy, gold, silver, aluminum, graphite, boron nitride, beryllium, magnesium, calcium, strontium, barium, lithium, rubidium, cesium, and a combination of any of the foregoing.

9. The method of claim 1, wherein said second material is selected from steel, stainless steel, carbon steel, nickel, nickel alloy, nickel-chromium and iron alloy, nickel-molybdenum-chromium alloy, polycrystalline nickel alloy, nickel-copper alloy, cobalt-chromium alloy, copper, copper alloy, zirconium, niobium, molybdenum, tantalum, tungsten, rhenium, platinum, platinum alloy, palladium, iridium, ruthenium, rhodium, osmium, titanium, vanadium, chromium, chromium alloy, iron, iron alloy, gold, silver, aluminum, and a combination of any of the foregoing.

10. The method of claim 1, wherein said first material is selected from copper, copper alloy, gold, silver, palladium, platinum, platinum alloy, iridium, ruthenium, rhodium, osmium, titanium, vanadium, chromium, chromium alloy, iron, iron alloy, nickel, nickel alloy, zirconium, niobium, molybdenum, tantalum, tungsten, rhenium, and a combination of any of the foregoing.

11. The method of claim 1, further comprising providing a first fluid disposed between the process capsule and the support capsule, or providing a second fluid disposed between the support capsule and a pressure apparatus, the first fluid and the second fluid independently selected from air, oxygen, hydrogen, ammonia, argon, water, nitrogen, helium, nitrous oxide, carbon dioxide, methane, ethane, propane, ethylene, propylene, methanol, isopropanol, acetic acid, benzene, toluene, ethanol, acetone, and a combination of any of the foregoing.

12. The method of claim 1, further comprising disposing a baffle between a first region of the interior volume and a second region of the interior volume.

13. The method of claim 1, further comprising forming of a wafer from the crystalline material.

14. The method of claim 13, further comprising forming a device on the wafer.

15. The method of claim 1, wherein said second material is less expensive than said first material.

16. The method of claim 1, wherein the wall thickness of said support capsule is greater than the wall thickness of said process capsule.

17. The method of claim 1, wherein said process capsule comprises a fill tube extending from a first open end through which the fluid is passed to fill an interior volume of the process capsule.

18. The method of claim 17, wherein sealing comprising pinching said fill tube.

19. The method of claim 1, wherein loading said at least one fluid is performed at below room temperature.

20. The method of claim 1, wherein said at least one fluid expands said process capsule at room temperature.

21. The method of claim 1, wherein said second material is less inert than said first material to the supercritical fluid.

22. The method of claim 1, wherein the second material has a higher yield strength than the first material.

23. The method of claim 1, wherein the second material has a higher Young's modulus than the first material.

24. The method of claim 1, wherein the process capsule is mechanically coupled to a wall of the support capsule.

* * * * *

UNITED STATES PATENT AND TRADEMARK OFFICE
CERTIFICATE OF CORRECTION

PATENT NO. : 10,029,955 B1
APPLICATION NO. : 13/657551
DATED : July 24, 2018
INVENTOR(S) : Pakalapati Tirumala Rajeev et al.

It is certified that error appears in the above-identified patent and that said Letters Patent is hereby corrected as shown below:

On the Title Page

In the Inventor names:
Item [72], Inventors: replace First name inventor "Pakalapati Tirumala Rajeev" with --Rajeev Tirumala Pakalapati--.

In the Claims

Column 20, Lines 22-25, Claim 2: replace "The method of claim 1, wherein the crystalline material comprises a [III-]nitride of a croup III element of the periodic table selected from GaN, AlN, InN, an alloy of any of the foregoing, and a combination of any of the foregoing" with --The method of claim 1, wherein the crystalline material comprises a nitride of a group III element of the periodic table selected from GaN, AlN, InN, an alloy of any of the foregoing, and a combination of any of the foregoing--.

Signed and Sealed this
Eleventh Day of June, 2019

Andrei Iancu
*Director of the United States Patent and Trademark Office*